United States Patent [19]

Charles et al.

[11] 4,118,280
[45] Oct. 3, 1978

[54] AUTOMATED MICROBIAL ANALYZER

[75] Inventors: Ronald A. Charles, St. Louis County; Paul W. Jones, St. Charles; John L. Staples, Florissant; Joseph R. Wiegner, Ballwin, all of Mo.

[73] Assignee: McDonnell Douglas Corporation, St. Louis, Mo.

[21] Appl. No.: 682,664

[22] Filed: May 3, 1976

[51] Int. Cl.² ........................................... C12K 1/04
[52] U.S. Cl. ................................. 195/127; 250/328; 353/25; 353/117; 356/244; 422/64
[58] Field of Search .................... 195/127; 23/253 R; 356/244; 250/328; 353/25, 53, 117

[56] References Cited

U.S. PATENT DOCUMENTS

| 2,375,706 | 5/1945 | Stechbart et al. | 353/117 |
|---|---|---|---|
| 2,949,815 | 8/1960 | Rosenberger et al. | 353/53 |
| 3,152,509 | 10/1964 | Zillmer | 353/53 |
| 3,179,007 | 4/1965 | Benford | 353/53 |
| 3,193,684 | 7/1965 | Kingston | 250/328 |
| 3,554,639 | 1/1968 | Robinson | 353/117 |
| 3,704,953 | 12/1972 | Carter et al. | 356/244 X |
| 3,776,817 | 12/1973 | van der Pfordten | 195/127 X |
| 3,851,972 | 12/1974 | Smith et al. | 356/244 X |
| 3,902,799 | 9/1975 | Winkler et al. | 353/117 X |
| 3,928,140 | 12/1975 | Wyatt et al. | 195/127 X |

Primary Examiner—Raymond N. Jones
Assistant Examiner—Robert J. Warden
Attorney, Agent, or Firm—Gravely, Lieder & Woodruff

[57] ABSTRACT

Medical specimens suspected of containing harmful microorganisms are diluted in saline solution and the dilution so formed is vacuum loaded into a cuvette or card containing viewing walls having dried selective culture media therein. The dilution rehydrates the culture media, each of which is selective in the sense that its optical characteristics will change when the organism to which it is specific metabolizes within it. A plurality of the cards are loaded into a tray, and the tray is placed on a rotatable carrousel of a card holder unit along with other trays. The carrousel is indexed at periodic intervals, and each time that it is indexed a different tray moves to a reading position facing a card reader unit. The carrousel has a center stack from which heated air is discharged such that it passes along both major surface areas of the cards in the tray, thus maintaining the cards at a temperature suitable for incubating microorganisms in them. The reader unit includes a reader head which moves vertically along that tray which is in the reading position, and this head has extractor and locator slides which move horizontally. The extractor slide engages each card and withdraws it individually from the tray, while the locator slide, which is spring loaded with respect to the extractor slide, bears against the card as it is withdrawn so as to maintain it in the proper orientation with respect to arrays of light emitters and corresponding detectors on the reader head. The emitters and detectors are arranged in pairs, with the detector of each pair being illuminated by the emitter, unless otherwise obscured. The card as it is withdrawn by the extractor slide moves between the pairs of emitters and detectors, and as it does some of the pairs register with identification segments on the card while other pairs register with the viewing wells. The former "read" identification numbers marked on the card with opaque ink, while the latter determine the light transmitting characteristics of the wells, this being achieved by projecting the light from the emitters through the wells and measuring the intensity of the light falling upon the detectors. A change in the light transmitting characteristics of a well indicates the presence of the specific microorganism in the well. That change provides a unique signature for the specific microorganism.

40 Claims, 20 Drawing Figures

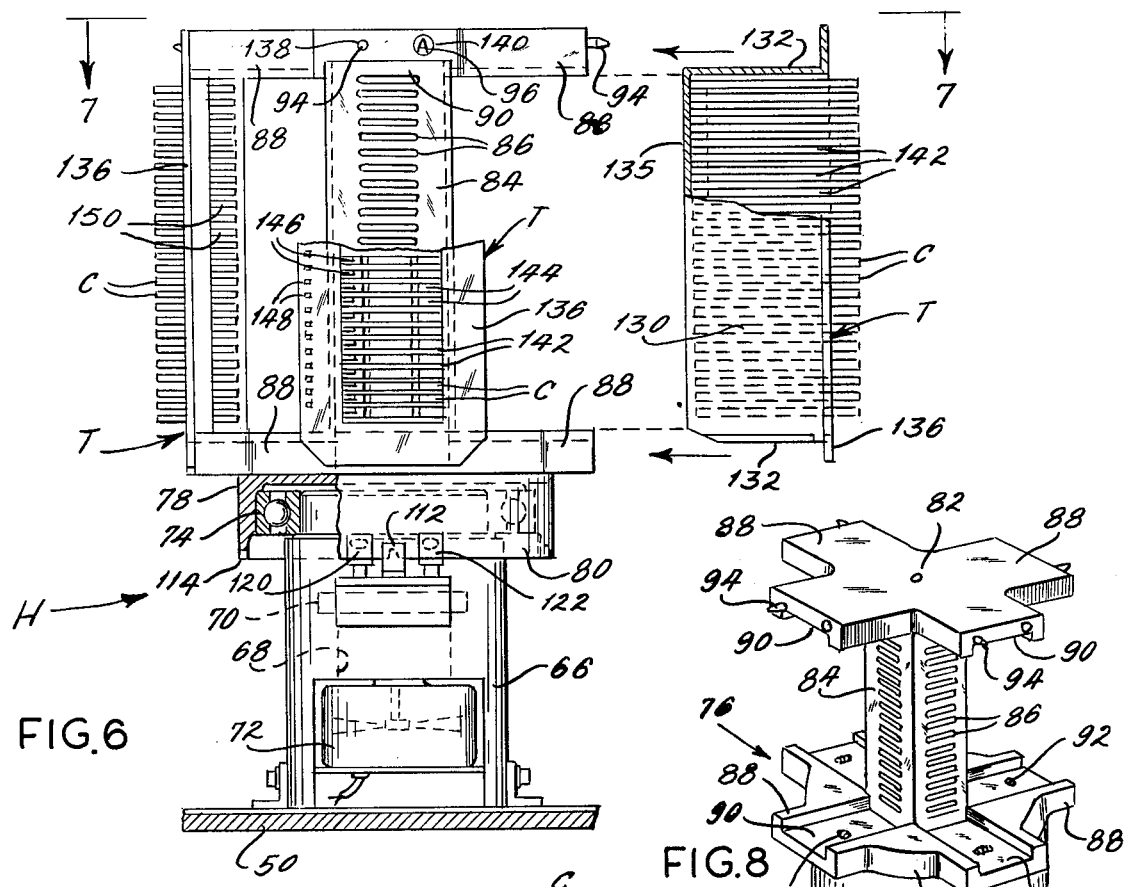
FIG. 6
FIG. 8
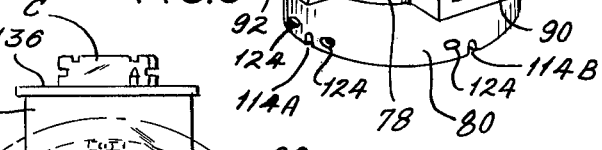
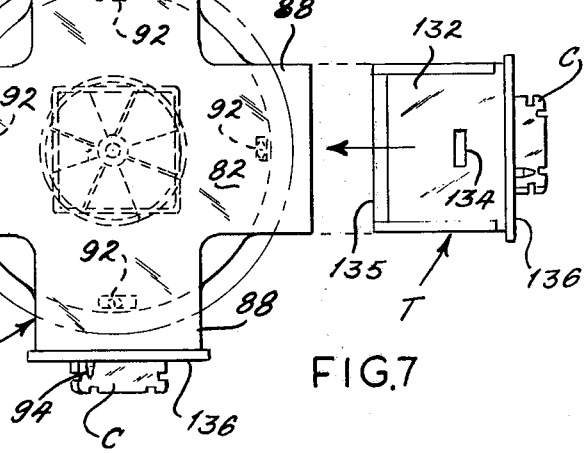
FIG. 7
FIG. 4

AUTOMATED MICROBIAL ANALYZER

BACKGROUND OF THE INVENTION

This invention relates in general to the detection of microorganisms, and more specifically to a machine for automatically analyzing specimens which have been introduced into media-containing cards so as to determine the presence of specific microorganisms in the card or to determine the effects of known antibiotics on such microorganisms.

The detection and identification of microorganisms is an important aspect of medical science which has heretofore been characterized by difficult and time consuming procedures requiring highly skilled personnel. For example, the conventional procedure for detecting and identifying a microorganism requires collecting a specimen on a swab and then wiping the swab over a nutrient surface. After incubating the culture medium for at least 24 hours, it is examined for pure colonies of microorganisms, but usually the initial incubation yields only a large biomass. A meaningful evaluation cannot be made until pure colonies are isolated, and this usually requires dilution and further incubation. Furthermore, it is often necessary to verify an identification by conducting biochemical tests on the isolated colonies. The time between sampling and identification typically ranges between two and three days.

When prescribing medicines and antibiotics, it is often necessary to know the identity of the microorganism causing illness. Indeed, the isolated colonies are subjected to various antibiotics to determine the susceptibility of the isolated microorganisms to the antibiotics. Current procedures do not provide an identification for several days, and usually the time expended in making the identification coincides with the most critical period of illness.

U.S. Pat. application Ser. No. 461,249 of C. Aldridge et al, filed Apr. 16, 1974, now U.S. Pat. No. 3,963,355 discloses a system for reducing the time required to identify microorganisms to about 13 hours or less. That system however is incapable of performing high volume screening.

SUMMARY OF THE INVENTION

One of the principal objects of the present invention is to provide a machine for automatically analyzing specimens for the purpose of detecting microorganisms therein with the analysis requiring not in excess of about 13 hours and for further determining the susceptibility of the microorganisms to various antibiotics. Another object is to provide a machine of the type stated which is capable of screening a high volume of specimens in excess of 100 per day. A further object is to provide a machine of the type stated which does not require the isolation of pure colonies of microorganisms for making an analysis. An additional object is to provide a machine of the type stated which for the successful operation thereof does not require highly skilled personnel trained in microbiology as do conventional procedures. Still another object is to provide a holder unit capable of holding many cards containing specimens while incubating the cards, and further having an indexing capability which enables it to place the cards in a reading position at periodic intervals. Yet another object is to provide a reading unit capable of extracting cards individually from an arrangement of cards and "reading" the cards when they are extracted. These and other objects and advantages will become apparent hereinafter.

The present invention is embodied in a machine including a moving element for extracting cards from a holder, light emitting means for projecting light through wells in the cards, and light detecting means for determining the intensity of the light passing through the wells. The invention also includes the combination of a holder for holding a plurality of cards, extracting means for withdrawing the cards individually from the holder, and reading means for monitoring viewing wells in the cards as they are withdrawn to ascertain any changes in light transmitting characteristics. In addition, the invention is embodied in a holder including a pedestal, a carrousel mounted on the pedestal, and means on the carrousel for holding cards in rows parallel to the axis of rotation.

DESCRIPTION OF THE DRAWINGS

In the accompanying drawings which form part of the Specification and wherein like numerals and letters refer to like parts wherever they occur:

FIG. 4 is a perspective view of a loading device utilized to introduce a specimen into the card;

FIG. 6 is an elevational view of the holder unit taken along line 6—6 of FIG. 5, and showing the base of its carrousel partially broken away and in section;

FIG. 7 is a plan view of the holder unit taken along line 7—7 of FIG. 6;

FIG. 8 is a perspective view of the carrousel forming part of the holder unit;

DETAILED DESCRIPTION

Figure 1:
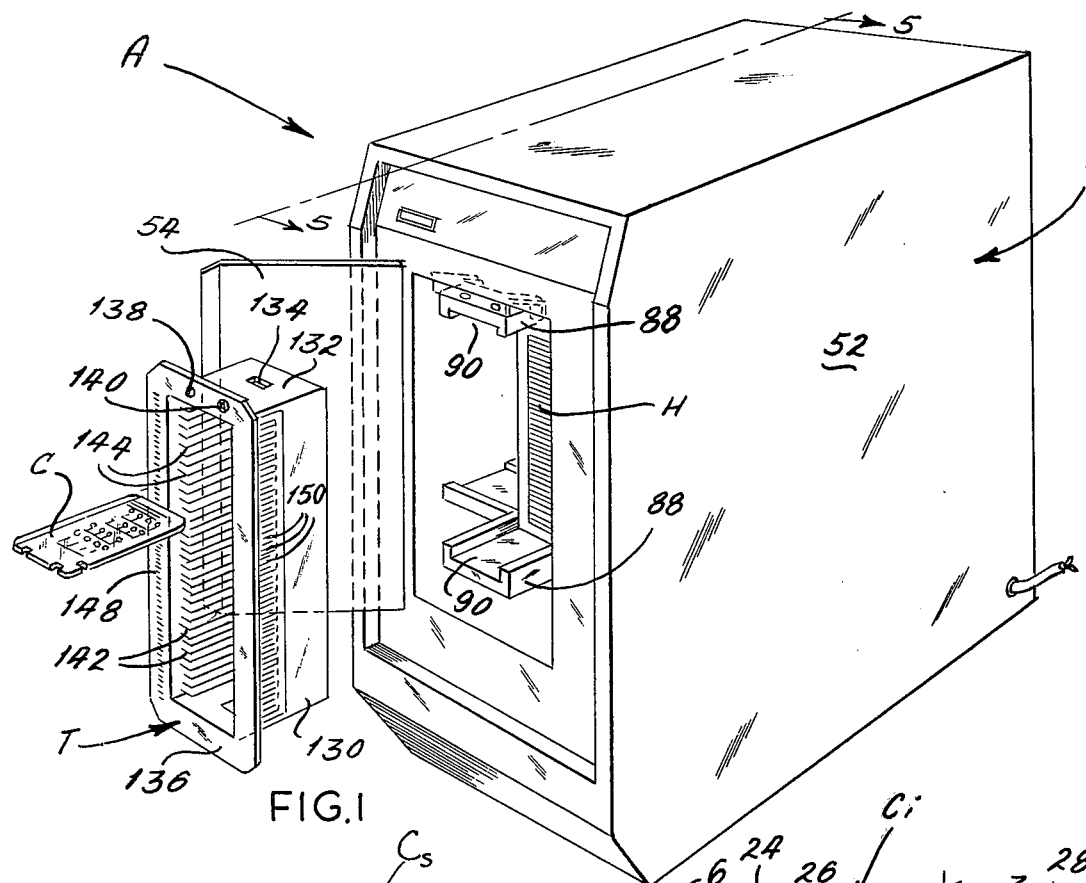
FIG. 1 is a perspective view of the automated microbial analyzer of the present invention with a tray thereof being removed from the holder unit and a card withdrawn from the tray.

Referring now to the drawings, a machine known as an automated microbial analyzer A (FIG. 1) is utilized to examine a multitude of cards C into which specimens suspected of containing harmful microorganisms have been introduced. The cards C contain dried selective media which is rehydrated by a sample of diluted specimen. If the specimen contains a microorganism to which a medium within the card C is specific, then the optical characteristics of the rehydrated medium will change as the microorganism metabolizes within the medium. The machine A detects the change in optical characteristics and hence indicates the presence of specific microorganisms.

Figure 5:
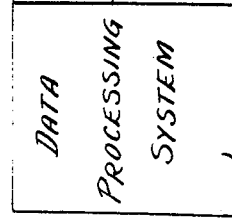
FIG. 5 is a sectional view taken along line 5—5 of FIG. 1 and showing the holder unit and reader unit of the analyzer in side elevation.

The machine A includes a cabinet D which houses a card holder unit H as well as a card reader unit R (FIG. 5). The holder H includes four trays T which are detachable therefrom, and each tray holds the multitude of cards C in sequence. The holder unit H further incubates the cards C while they are stored therein, and indexes at periodic intervals so as to bring the trays T successively to a reading position opposite the card reader unit R. The card reader unit R withdraws the cards C individually from the trays T of the holder assembly H, and ascertains identification marking on the cards C as they are withdrawn. It further replaces the cards C and in so doing projects light through the various rehydrated culture media within the cards C to detect changes in the optical characteristics of the rehydrated media. Such changes indicate metabolic activity and hence microorganisms in the media. Each card C is read every time the holder unit H brings the tray T for that card C to the reading position. The readings derived from the card reader unit R are introduced into a computer K which organizes and records them so as to provide a thorough analysis of each card C. The computer K also controls the operation of the reader unit R and the indexing of the holder unit H.

The Cards

Figure 2A:
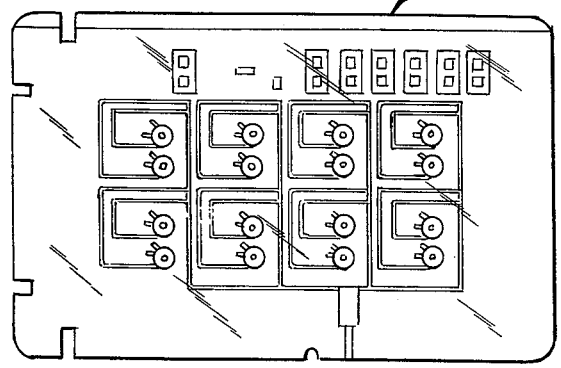
FIG. 2A is a plan view of the susceptibility card used to determine the effects of antibiotics on microorganisms identified with the identification card.

Two general types of cards C are handled by the analyzer A, one being an identification card $C_i$ (FIG. 2) and the other being an antibiotic susceptibility card $C_s$ (FIG. 2A). The identification card $C_i$ is used to identify microorganisms in the specimen which is introduced into it, while the susceptibility card $C_s$ is used to ascertain the effect of antibiotics on microorganisms identified with the card $C_i$. Both cards $C_i$ and $C_s$ have identical peripheral configurations and hence will for the most part be described merely as the card C.

The major component of the card C is a clear plastic plate 2 (FIGS. 2 & 3) possessing a rectangular configuration. Preferably the plate 2 is 3.59 inches long, 2.24 inches wide, and 0.125 inches thick. Along its front margin, the plate 2 has two outwardly opening positioning notches 4 (FIG. 2), while along each of its side margins it is provided with a gripping slot 6. The slots 6 are located quite close to the front margin out of which the notches 4 open. Along one of the side margins, the plate 2 is provided with a kerf 8 which imparts a stepped configuration to the plate 2 at that side margin. The other side margin has a shallow retaining notch 9 opening out of it, as well as a pair of filling bores 10 which have elastomeric septa 12 fitted tightly into them. Each bore 10 in turn leads into a separate receiving chamber 14 and at the entrance to the chamber the bore 10 is reduced to provide a neck. The septum 12 of the bore 10 has its end forced slightly beyond the neck to prevent the septum 12 from being dislodged upon the withdrawal of a needle from it. The chambers 14 open out of the upper of the two major surface areas on the plate 2.

Figure 2:
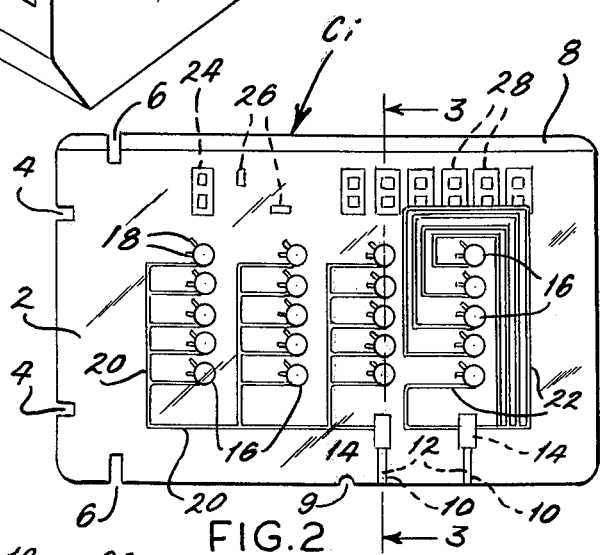
FIG. 2 is a plan view of an identification card into which diluted specimens are introduced to determine, upon examination by the analyzer, if specific microorganisms are in the specimen.
Figure 3:
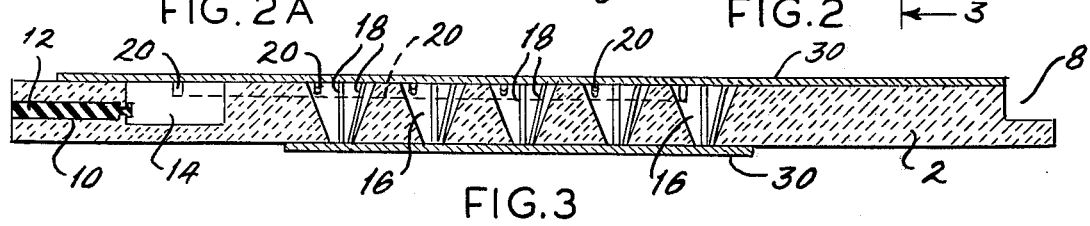
FIG. 3 is a sectional view of the identification card taken along line 3—3 of FIG. 2.

The plate 2 is further provided with a plurality of viewing wells 16 which are circular apertures extending completely through the plate 12. Each well 16 has a greater diameter at the upper surface of the plate 2 than at the lower surface, and in between possesses a frusto-conical shape (FIG. 3). The wells 16 are arranged in four rows with the rows extending transversely, that is parallel to the front and rear margins. Each well 16 has a pair of overflow channels 18 (FIG. 2) radiating from it toward the front margin, and these channels likewise extend completely through the plate 2. The wells 16 of the first three rows are connected to the first receiving chamber 14 by a filter channel 20 which is a narrow and shallow groove opening out of the upper surface of the plate 2. The branch leading into each well 16 is stepped slightly before the well 16 such that its shallowest depth is at the entrance to the well. Indeed, the depth at this point may be 0.010 inch while the width is 0.020 inch. The depth ahead of the step may be 0.020 inch. The channel 20 branches a slight distance beyond the first receiving chamber 14 and thereafter branches again so that a separate branch leads into each well 16. The branches isolate the wells 16 of the first three rows from each other, while the steps prevent wicking and migration of substances out of the wells 16. The wells 16 of the last row are connected to the second receiving chamber 14 through another filler channel 22 which likewise opens out of the upper surface of the plate 2 and is arranged to isolate the several wells 16 of that row from one another.

Adjacent to the kerf 8 the plate 2, on its underside, is provided with an identification segment 24 (FIG. 2) which is a very shallow indentation resembling the numeral 8 in block form. Thus, the segment 24 consists of a parallel top, intermediate, and bottom bars, as well as four side bars connecting the ends of the top, intermediate, and bottom bars. The segment 24 is stippled so that an ink marking placed on any one of its bars will distribute and adhere in a uniform manner. The segment 24 provides an outline in which a number may be marked. One or more code segments 26 are applied to the plate 2, these being opaque markings which align with the top, intermediate, or parallel bars of the segment 24 or at the upper or lower side bars. The code segments are utilized to identify the type of test for which the particular card C is designed. In the case of the identification cards $C_i$ a code segment 26 at one location may indicate that the particular card $C_i$ is for conducting an analysis on urine specimens, while a code segment 26 at another location may indicate that the card $C_i$ is for a throat specimen. Beyond the code segments 26 are a series of patient identification segments 28 which are arranged in a row parallel to the side edge of the card C. Each segment 28 resembles the block numeral 8 and is identical to the segment 24.

Most of and in some cases all of the viewing wells 16 contain a dehydrated culture media, and these media are selective in the sense that when rehydrated they will change the optical characteristics of the wells 16, but only when sustaining the particular microorganisms to which they are specific. For example, one well 16 may contain a culture medium which is specific to pseudomonas aeruginosa while another well 16 may contain culture medium which is specific to staphylococcus aureus. The change in optical characteristics is usually the result of increased turbidity or a change in color. Some of the wells 16 may be left empty or may contain a universal medium for purposes of control.

Each major surface area of the plate 2 is covered with a transparent tape 30 (FIG. 3) which is wide enough and long enough to completely extend over and close the ends of the viewing wells 16 and the ends of the overflow channels 18. The tape 30 on the upper surface area furthermore extends over and closes the receiving chambers 14 and the filter channels 20 and 22. Thus the tapes 30 together with the septa 12 isolate the receiving chambers 14, the viewing wells 16, the overflow channels 18, and the filter channels 20 and 22 from the surrounding atmosphere and prevent the entry of contaminants into the wells 16. The tapes 30 are slightly permeable in the sense that they will admit air to the wells 15, but the permeability is such that neither water nor microorganisms can escape from the wells 16. Furthermore, the tapes 30 admit air so slowly that they permit the interior of the wells 16 to be placed under a vacuum of at least 28 inches Hg and held at that condition for at least 3 minutes. FEP 5430 tape marketed by the 3M Company is suitable for the tapes 30.

The card C is loaded with a diluted specimen in a loading device L (FIG. 4) including a flat base 32, short and long tubes 34 and 36 projecting upwardly from the base 32 parallel to each other, and a pair of parallel guide webs 38 interposed between the base 32 and the short tube 34. The spacing between the webs 38 is slightly greater than the thickness of the card C so that the card C may be fitted between them. The tubes 34 and 36 have hollow needles 40 and 42 projecting radially from their lower ends and into the space between the webs 36. The spacing between the needles 40 and 42 equals the spacing between the bores 10 in the plate 2, while the distance between the lower needle 42 and the base 32 equals the distance between the lower needle 42 and the base 32 equals the distance between rear end edge on the card C and the rear filling bore 10. Hence, when the card C is inserted between the webs 36 with its rear edge resting on the base 32 and its filling bores 10 presented toward the tubes 34 and 36, the needles 40 and 42 will align with the septa 12.

To couple the card C with the loading device L, the card C is advanced toward the tube 34 until the needles 40 and 42 are projected through the septa 12. This provides communication between the interior of the tubes 34 and 36 and the interior of the card C. The upper end of each tube 34 and 36 is open and is fitted with a removable stack 44 containing a wad of cotton 46 which serves as a filter.

The specimen is diluted in 0.5% saline solution (NaCl) and the dilution so formed is placed in the short tube 34. A known volume of saline solution is placed in the long tube 36 and thereafter a known quantity of dilution is withdrawn from the short tube 34 by means of a pipette and released into the long tube 36, thus effecting a further dilution. Thereafter the stacks 44 are fitted over the tubes 34 and 36 and the loading device L and card C are placed in a vacuum chamber where the pressure is reduced to about 28 inches Hg. This causes air within the wells 16, the overflow channels 18, the filler channels 20 and 22, and the receiving chambers 14 to pass out of the card C through the needles 40 and 42 and to bubble through the dilution in the tubes 34 and 36. The vacuum is held for about 3 minutes and then released, permitting normal atmospheric pressure to again exist at the upper surface of this dilution. This forces the dilution through the needles 40 and 42 and into the receiving chambers 14 of the card C. The dilution continues through the filler channels 20 and 22 to the wells 16 where it mixes with and rehydrates the selective culture media in the wells 16. Any entrapped air migrates to the overflow channels 18, which are directed upwardly when the card is loaded.

The susceptibility cards $C_s$ (FIG. 2A) are quite similar to the identification cards $C_i$ except for the fact that they have fewer wells 16 and the filler channels 20 are arranged somewhat differently. Furthermore, all filler channels 20 lead to a single receiving chamber 14 and septa 12, so that the cards $C_s$ are filled with a loading device having only one tube 34 and needle 40. While the card $C_s$ has fewer wells 16 than the cards $C_i$, the wells 16 which do exist occupy locations which are exactly the same as the wells 16 of the card $C_i$. In other words, if the susceptibility card $C_s$ is placed over the identification card $C_i$, the wells 16 in both will be in registration. Also the selective media in the wells 16 of the susceptibility cards $C_s$ contain antibiotics. Of course, the code segments 26 are arranged differently to indicate not only that the card $C_s$ is for antibiotic sensitivity tests, but also to indicate the type of microorganisms for which the susceptibility test is designed. The susceptibility card $C_s$ is described in more detail in U.S. patent application Ser. No. 528,840, of Sandra F. Gibson and Norman L. Fadler, filed Dec. 2, 1974.

Selective culture media suitable for use in the cards C are disclosed in U.S. Pat. application Ser. No. 461,249 of C. Aldridge, Jr. et al, filed Apr. 16, 1974, now U.S. Pat. No. 3,963,355, as well as other applications filed contemporaneously herewith and assigned to the McDonnell Douglas Corporation. The same culture media when mixed with various antibiotics are suitable for use in the susceptibility card $C_s$.

The Cabinet

The cabinet D includes a rigid metal base plate 50 (FIG. 5) and a rectilinear closure 52 which fits onto the base plate 50. One end wall of the closure 52 is provided with a door opening over which a hinged door 54 fits. When opened, the door 54 provides access to the interior of the closure 52. The door 54 is retained in its closed position by a solenoid lock 56 which, upon being energized, engages a keeper 58 on the door 54. The same end wall has a "read" light 60 (FIG. 1) which is illuminated when the solenoid lock 58 is energized and the door 54 is locked.

The Card Holder Unit

The card holder unit H (FIGS. 5-9) is located within the cabinet D immediately beyond the door 54 and in front of the card reader assembly R. It is accessible when the door 54 is open (FIG. 1). The holder unit H includes a pedestal 66 (FIGS. 5 & 6) which is fastened securely to the base plate 50 of the cabinet D. The pedestal 66 has a hollow interior which forms a central upwardly opening cavity 68 having a heater element 70 of the electrical resistance variety within it. Below the element 70, the pedestal 66 supports a fan 72 which directs an airstream upwardly through the cavity 68 and across the heater element 70. At its upper end, the pedestal 66 is fitted to the inner race of a bearing 74 having a vertical axis of rotation which is centered with respect to the cavity 68. The bearing 74 is capable of carrying thrust as well as radial loading.

In addition to the pedestal 66, the card holder unit H includes a carrousel 76 (FIGS. 5 & 6) which rotates on the pedestal 66. The carrousel 76 includes a base 78 in which the outer race of the bearing 74 is received, to enable the carrousel 76 to rotate freely. The base 78 has a downwardly extending skirt 80 which encircles the upper end of the pedestal 66. The outer surface of the skirt 80 is perfectly cylindrical and concentric to the axes of the bearing 74.

The base 78 for the carrousel 76 is located below a cap 82 (FIG. 8), and the two are connected by a stack 84 which is square in cross section. The hollow interior of the stack 84 aligns and communicates with the central cavity 68 in the pedestal 66 so that the upwardly directed airstream which is generated by the fan passes outwardly through horizontal slots 86 in the four walls of the stack 84. Each wall of the stack 84 has a plurality of slots 86 arranged one after the other in the vertical direction at equally spaced intervals. The cap 82 closes the upper end of the stack 84.

Both the base 78 and the cap 82 of the carrousel 76 have four retaining arms 88 which are spaced at 90° intervals with the arms 88 on the cap 82 being located directly above the arms 88 on the base 78. Moreover, the arms 88 are oriented such that they project outwardly from the four walls of the stack 84, that is, they are oriented perpendicular to the walls of the stack 84. Thus, the heated airstream as it is discharged through the slots 86 in the stack 84 passes between the four pairs of retaining arms 88 on the carrousel 76. Each arm 88 has a retaining groove 90 which extends the full length thereof, with the grooves 90 of upper arms 88 opening downwardly and the grooves 90 of the lower arms 88 opening upwardly. Each retaining arm 88 at the base of its groove 90 is fitted with a spring loaded roller detent 92, the roller of which projects a slight distance into the groove 90. Moreover, the upper retaining arms 88 at their ends have outwardly directed locating pins 94 provided with tapered ends. Each upper arm 88 is further provided with an identification button 96 which is located on the end face of the arm 88. These buttons are assigned letters A, B, C and D to distinguish the four pairs of arms 88 from each other.

The trays T fit between the pairs of retaining arms 88 (FIG. 6) and are retained in place by the detents 72. They take the letter designation of the pairs of retaining arms 88 between which they are located. Since the pairs of retaining arms 88 are at 90° intervals, one tray T will be located in a reading position opposite the reader unit R when another tray T is presented in a loading position opposite to the door 54 in the cabinet D (FIG. 5). The two remaining trays T will, of course, be presented laterally toward the side walls of the cabinet D.

The carrousel 76 is rotated by a capstan drive 98 (FIG. 5) which is mounted on the pedestal 66. The rotation is of an incremental nature, with each increment being 90°. This brings succeeding pairs of retaining arms 88, and the trays T between them, to the reading position opposite the reader unit R. The capstan drive 98 includes a D.C. stepping motor 100 which is mounted on a gear box 102, which in turn pivots about a vertical pintle 104 located in a fixed position on the side of the pedestal 66. The gear box 102 rotates a drive shaft 106 extending upwardly out of it, and this shaft at its upper end is fitted with a rubber drive wheel 108 which is located opposite the cylindrical surface on the skirt 80 of the carrousel 76. The drive wheel 108 is urged against the skirt 80 by a spring 110 which is extended between the gear box 102 and the pedestal 66. Hence, when the motor 100 is energized, it rotates the drive shaft 106 and drive wheel 108, and the drive wheel 108 turns the carrousel 76. The connection between the drive wheel 108 and the skirt 80 of the carrousel 76 is of a purely frictional nature.

The motor 100 of the capstan drive 98 is controlled by an optical switch 112 (FIGS. 5 & 6) located on the opposite side of the pedestal 66. The switch 112 is connected to the computer K and senses notches 114 located in the cylindrical skirt 80 beneath the arms 88. The notches 114 are located at 90° intervals around the skirt 80. The optical switch 112 includes a light emitting diode 116 (FIG. 5) and a phototransistor 118. The light emitting diode 116 is located opposite the exterior surface of the skirt 80 and is directed inwardly, whereas the phototransistor 118 is located within the skirt 80 and is directed outwardly, it being aligned with the diode 116. Moreover, the diode 116 and transistor 118 are positioned such that the light emitted by the former is interrupted by the skirt 80, except when a notch 114 in the skirt 80 is between the diode 116 and transistor 118. The circuitry is such that the motor 100 will operate as long as the light emitted by the diode 116 is interrupted by the skirt 80, but once the transistor 118 is illuminated by the diode 116, the motor 100 will cease to operate, and the carrousel 76 will stop. This latter event occurs each time one of the notches 114 comes between the diode 116 and transistor 118. The motor 100 is initially energized by the computer K, and the optical switch 112 provides the signal which causes the computer K to stop the motor 100, with the control being such that the motor 100 is energized once every 15 minutes. Thus, the carrousel 76 indexes 90° every 15 minutes.

Figure 9:
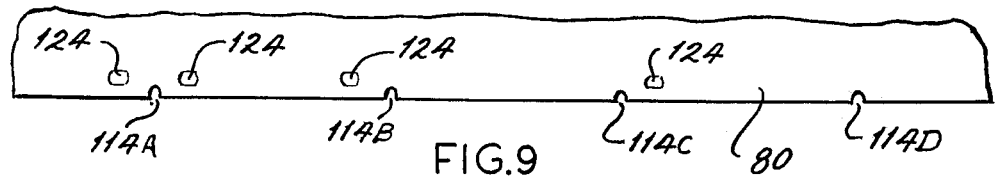
FIG. 9 is a fragmentary view taken along line 9—9 of FIG. 7 and showing the skirt on the carrousel, with that skirt being opened up into a plane to illustrate all the locating notches and positioning apertures therein.

The optical switch 112 is located between two optical position switches 120 and 122 (FIG. 6) each of which is composed of a light emitting diode located outside the skirt 80 and an aligned phototransistor located within the skirt 80. These switches 120 and 122 are also connected with the computer K and enable the computer K to determine the position of rotation by directing light through apertures 124 in the skirt 80, these apertures being located adjacent to the notches 114 in various arrangements (FIG. 9). For example, when the carrousel 76 is at rest with arms 88A (those arms designated by the identification button 96 bearing the letter A) located opposite the reader unit R, an aperture 124 will be at both optical switches 120 and 122 and the phototransistors of both will conduct. The condition in which both phototransistors conduct indicates that the arms 88A are in the reading position. However, at the notch 114B for the arms 88B, only one aperture 124 exists, it being to the left of the notch 114B. Thus, only the switch 120 will conduct, indicating that the arms 88B are in the reading position. The notch 114C for the arms 88C likewise has only one aperture 124, but it is located to the right of the notch 114C so that only the switch 122 conducts when the arms 88C are located in the reading position. Finally, the notch 114D for the arms 88D has no apertures 124 next to it so that neither of the switches 120 and 122 conduct when the arms 88D are opposite to the reader unit R.

The carrousel 76 is free to rotate when the door 54 of the cabinet D is closed, but when the door 54 is opened, it releases a bifurcated retaining element 126 (FIGS. 5 & 10) which is hinged to the front wall of the closure 52 such that it pivots about a horizontal axis. The element 126 has a tab 127 which is engaged by the door 54 when the door 54 is closed, and when so engaged the element 126 is held upwardly. However, when the door 54 is opened, the element 126 swings downwardly and the tines thereof pass on each side of that upper retaining arm 88 which is presented toward the door 54. This prevents rotation of the carrousel 76. The retaining element 126 also has an arm 127 which moves with the element and the position of the arm 127a is sensed by an optical switch 127b on the front wall of the cabinet D. The switch 127b is connected with the computer K so that the computer will not energize the capstan drive 98 for the carrousel 76 when the element 126 is down and the door 54 is open. The solenoid lock 58 remains energized while the carrousel 76 is indexing and also while the reading device is reading cards C so that the door 54 cannot be opened during these times.

The temperature of the airstream passing through the stack 84 is monitored by a thermocouple probe 128 (FIG. 5) which projects into the stack 84 through the cap 82 of the carrousel 76. The probe 128 is carried by a bracket 129 which is attached to the front wall of the closure 52. The probe 128 controls the heater element 70 to maintain a substantially constant temperature in the airstream.

The trays T, as previously noted, constitute a part of the holder unit H, there being one tray T between each of the four pairs of retaining arms 88. Each tray T is molded as an integral unit from a suitable plastic and includes side walls 130 (FIG. 1) which are connected by end walls 132 in a rectangular configuration. The spacing between the side walls 130 is slightly less than the width of the grooves 90 in the retaining arms 88, while the spacing between the end walls 132 is slightly less than the spacing between opposed upper and lower arms 88 at the bases in the grooves 90 of those arms. Thus, the tray T will fit between a pair of retaining arms 88 with its upper and lower ends being received in the grooves 90. Both end walls 132 have apertures 134 into which the spring loaded detents 92 fit, and this maintains the tray T in place on the carrousel 76. When the tray T is so disposed, its back will be at the stack 84. Along the side walls 130, the back of the tray T is closed by back walls 135 (FIG. 19). but the remainder of the back is completely open so that the heated air discharged from the slots 86 in the stack 84 will pass through the tray T. The front of the tray T is also open and is surrounded by a front flange 136 which projects outwardly from the front margins of the side and end walls 130 and 132. The upper portion of the flange 136 has a circular hole 138 (FIGS. 1 & 6) through which the locating pin 94 on the upper retaining arm 88 projects. This properly positions the tray T between the two arms 88. The upper portion of the flange 136 is further provided with a circular viewing aperture 140 through which the identification button 96 on the upper returning arm 88 is exposed.

Figure 13:
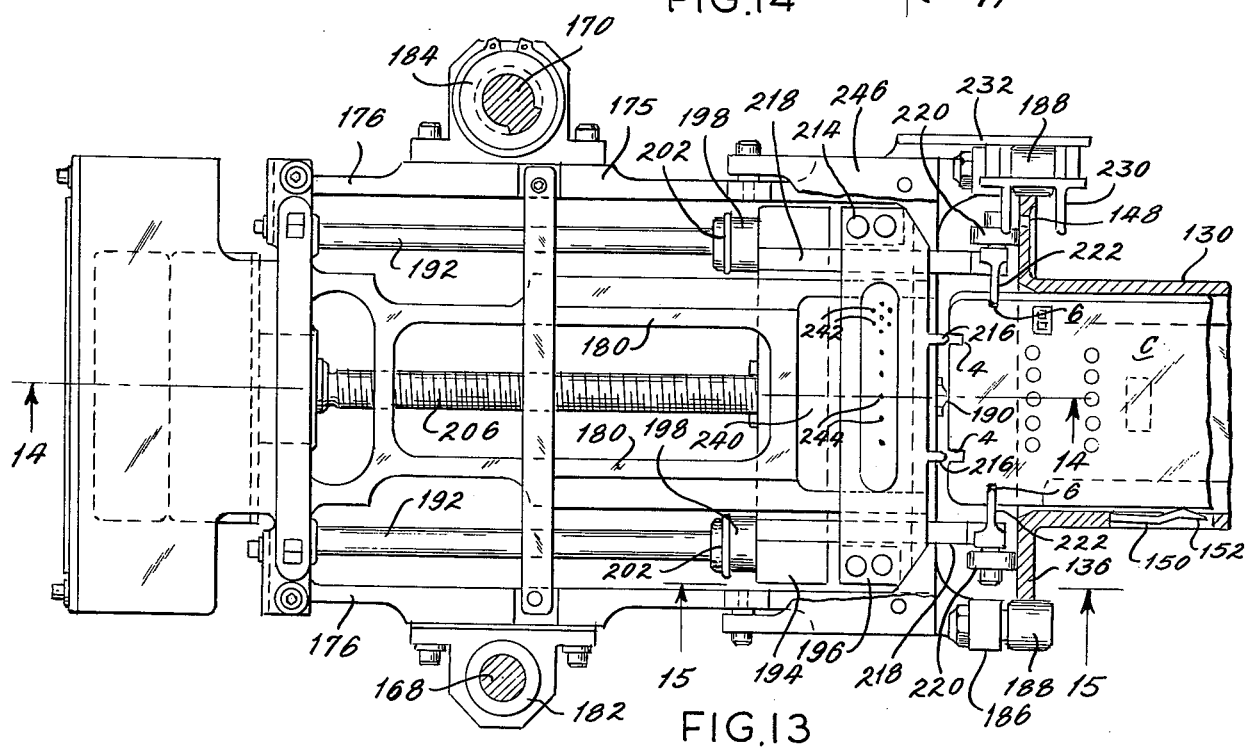
FIG. 13 is a plan view of the reading head showing the extractor and locator slides aligned with a card in the tray prior to the extraction of the card.

The spacing between the interior faces of the side walls 130 is slightly greater than the width of the cards C, and on these inside faces the walls 130 are provided with a series of fins 142 (FIGS. 6 & 19) which extend from front to rear and form card receiving slots 144 in the tray T. The spacing between adjacent fins 142 is slightly greater than the thickness of the individual cards C, so that the cards C are easily inserted into and withdrawn from the slots 144. The depth of the tray T is such that when a card C is fully inserted all the way to the back wall 135, the gripping slots 6 at the sides of the card C will still be located somewhat beyond the front flange 136 (FIG. 7). Moreover, when the tray T is installed between the arms 88 the fins 142 align with the horizontal slots 86 in the stack 84, or in other words the card receiving slots 144 are offset from the air discharge slots 86. As a result, the heated air discharged from the slots 86 in the stack 84 passes over both major surface areas of each card C. The channels between adjacent cards C are less restrictive to the flow of air than the slots 86 in the stack 84 so the volume of the air flow remains constant irrespective of whether or not cards C are in the tray T. Each fin 142 along the left side wall 130 has a key 146 (FIGS. 5 & 6) extended along its underside. The key 146 will interfere with the squared off side edge, but not the side edge containing the kerf 8, that is the key 146 will be received in the kerf 8 of the card C. Thus, the cards C will fit into the card receiving slots 144 with only one orientation, that being when the positioning notches 4 and gripping slots 6 are located beyond the front flange 136 and the identification segments 24, 26, 28 are located along the left side of the card C (FIGS. 7 & 13).

The Reader Unit

The reader unit R (FIGS. 5 & 11) is located within the cabinet D beyond the card holder unit H and faces those arms 88 of the carrousel 76 which are in the reading position. Thus, the carrousel 76 must index twice, that is 180°, before a tray T loaded on a pair of arms 88 at the door 54 reaches the reading unit R. The cards C of this tray T are withdrawn individually by the reading unit R which optically "reads" the viewing wells 16 and the numbers and other indicia in the segments 24, 26, and 28. Each card C is replaced into the tray T before the next card C is withdrawn and read.

The card reader unit R includes a main frame 160 (FIGS. 5 and 11) which is attached firmly to the base plate 50 of the cabinet D. The frame 160 includes a pair of upright members 162, the upper ends of which are connected by a top piece 164. The frame 160 also includes a cross piece 166 which extends between the upright members 162 quite close to the base plate 50. Extended between the top piece 164 and the cross piece 166 are a vertical guide rod 168 and a vertical drive screw 170, with the former being adjacent to the one upright member 162 and the other being adjacent to the other upright member 162. At its ends the drive screw 170 has journals which revolve in bearings on the top piece 164 and cross piece 166. The screw 170 is rotated by a D.C. stepping motor 172 which is mounted on the cross piece 166, and this stepping motor is reversible and controlled by the computer K.

Figure 11:
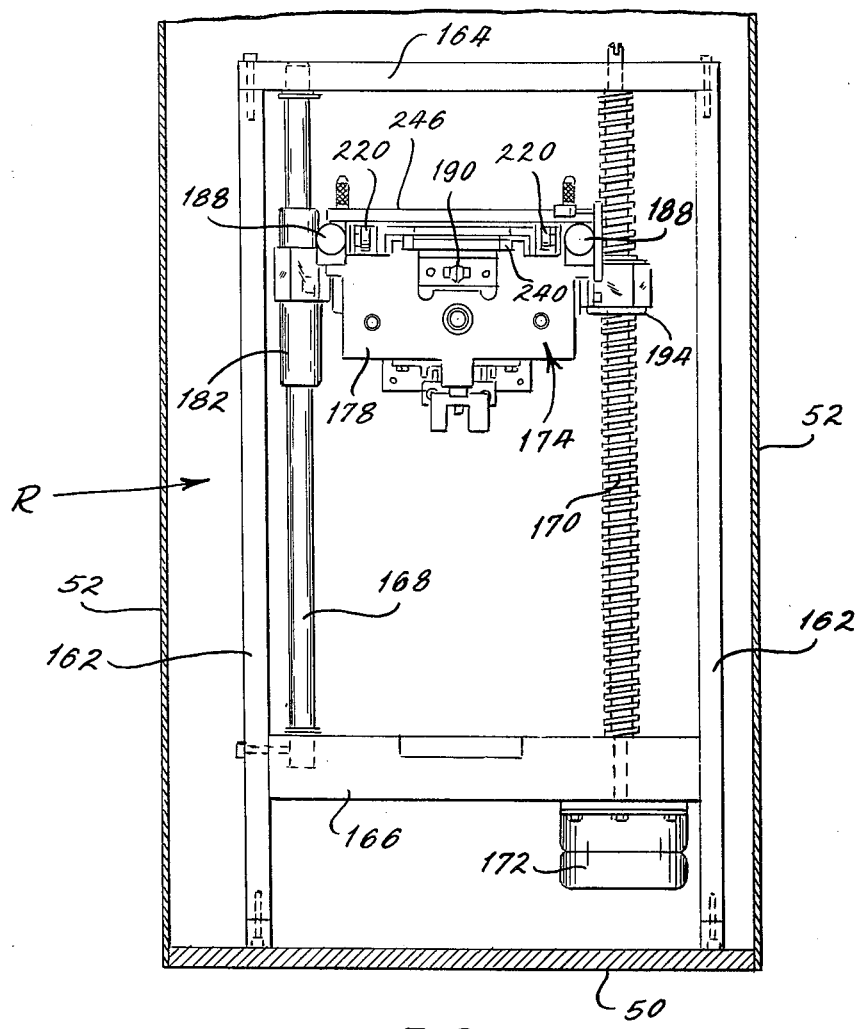
FIG. 11 is a front elevational view of the reader unit taken along line 11—11 of FIG. 5.
Figure 12:
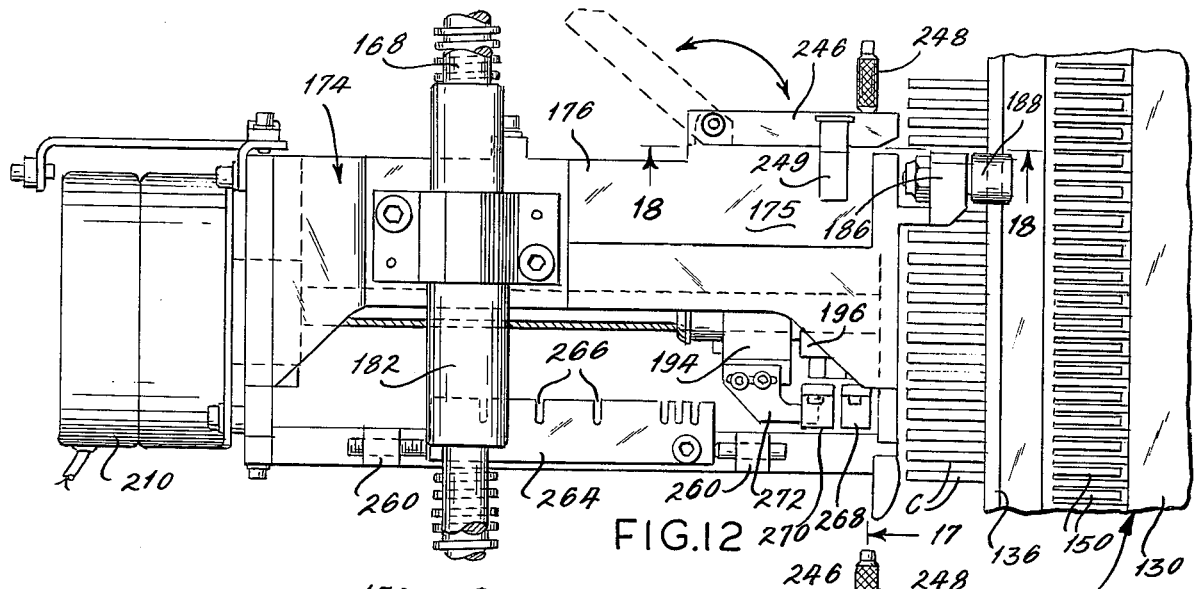
FIG. 12 is a side elevational view of the reading head on the reader unit.
Figure 19:
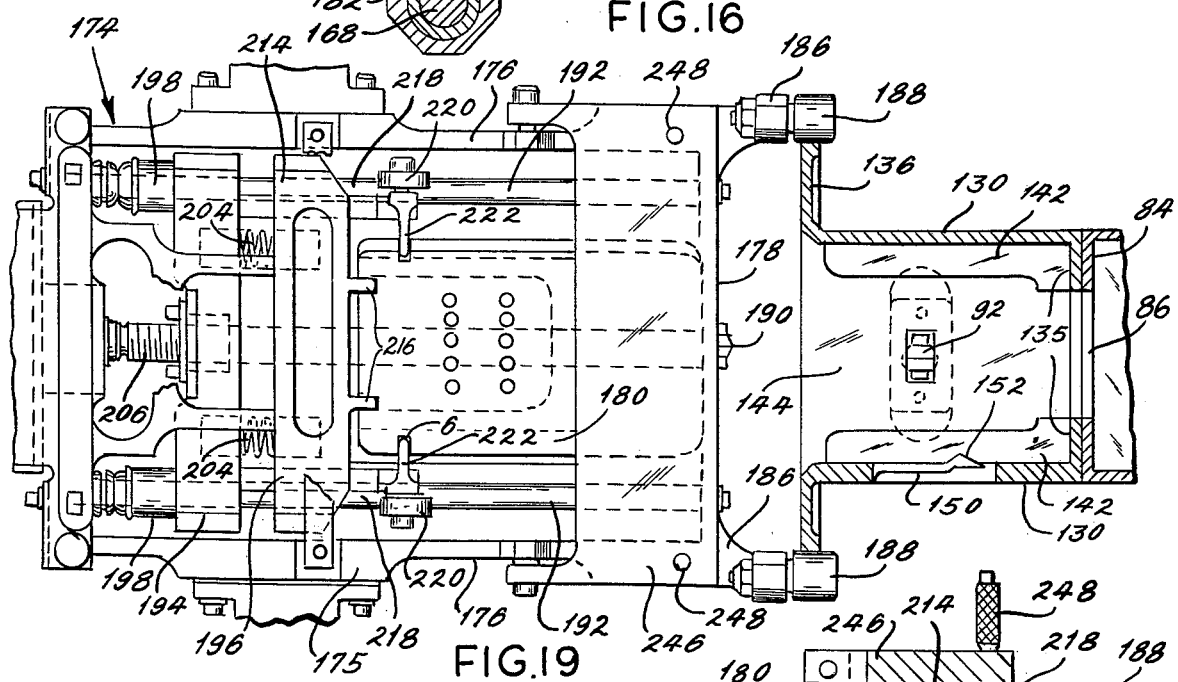
FIG. 19 is a plan view of the reading head showing a card extracted by the extractor and locator slides of the head for the purpose of reading the card.
Figure 18:
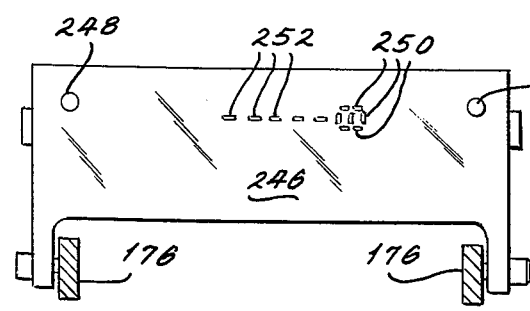
FIG. 18 is a sectional view taken along line 18—18 of FIG. 12 and showing the underside of the upper dielectric plate of the reader head.

Both the drive screw 170 and the guide rod 168 extend through a reader head 174 (FIG. 11) with the screw 170 being connected such that when it revolves in one direction, the head 174 will ascend, and when it revolves in the opposite direction, the head 174 will descend. More specifically, the reader head 174 includes a mounting element or block 175 (FIGS. 12-14) comprised of parallel side walls 176, parallel front and rear end walls 178 and a top wall 180, all joined together with the front end wall 178 being presented toward the card holder unit H. One side wall 176 has a bushing 182 attached to it and the guide rod 168 extends through the bushing 182 (FIG. 11). The other side wall 176 has a nut 184 attached to it and the vertical drive screw 170 threads this nut 184. Thus, rotation of the screw 170 will cause the reader head 174 to move upwardly or downwardly, depending on the direction of rotation. At its forward end, the main block 175 is provided with a pair of lugs 186 on which side rollers 188 are mounted. The rollers 188 are free wheeling and the spacing between them is only slightly greater then the width of the tray T at the front flange 136 thereon (FIG. 19). Indeed, the rollers 188 are positioned forwardly enough to pass along the side edges of the front flange 136 as the block 176 ascends and descends, thus keeping the tray T oriented properly in the reading position. When the reading head 174 is elevated to the top of the frame 160, the side rollers 188 are above the flange 136, and this frees the tray T so that the carrousel 76 of the holder H may be indexed (FIG. 5). On its front end wall 178, the main block 175 is provided with a positioning roller 190 (FIGS. 11 & 13) which passes across the front edges of the cards C between the positioning notches 4 therein and insures that all cards C are in their fully inserted positions. Any card C which is not in that position will be forced into the tray T by the roller 190 as the head 174 descends.

Figure 16:
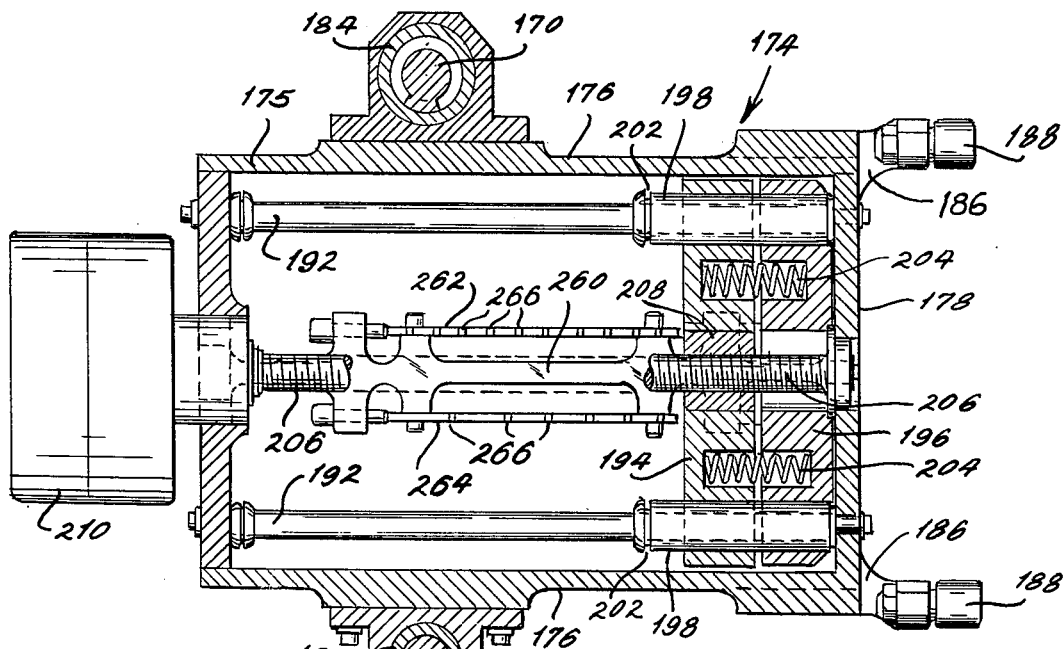
FIG. 16 is a sectional view of the reader head taken along line 16—16 of FIG. 14.

Extended between the front and rear end walls of the main block 175 are a pair of parallel slide rods 192 (FIGS. 13 & 16), and these rods are further parallel with the card receiving slots 144 of that tray T which is in the reading position. The rods 192 in turn support an extractor slide 194 and a locator slide 196 with the former being located for the most part to the rear of the latter. In particular, the locator slide 192 has sleeves 198 fitted tightly into it and the slide rods 192 extend through the sleeves 198, enabling the locator slide 196 to move horizontally on the main block 175 toward and away from the front wall 178. The sleeves 198 project rearwardly through the extractor slide 194 so that the extractor slide 194 in effect moves over the sleeves 198, while the locator slide 196 moves over the slide rods 192. The sleeves 198 extend completely through the extractor slide 194, beyond which they are fitted with ring-type clips 202 which serve as a stop to limit the distance that the two slides 194 and 196 may be separated. The two slides 194 and 196 are urged apart by two compression type coil springs 204 which are interposed between them (FIG. 16).

Figure 14:
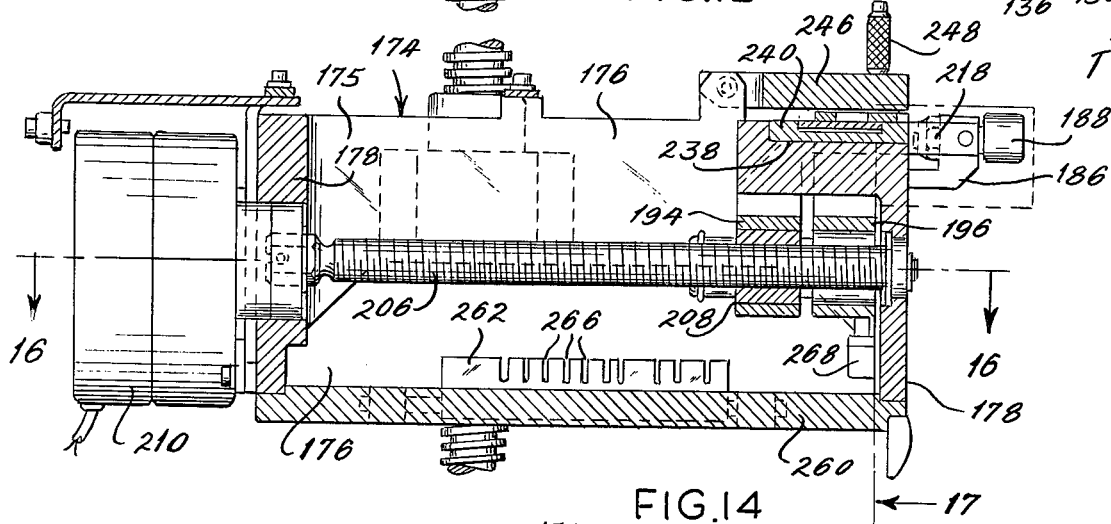
FIG. 14 is a sectional view of the reading head taken along line 14—14 of FIG. 13.
Figure 15:
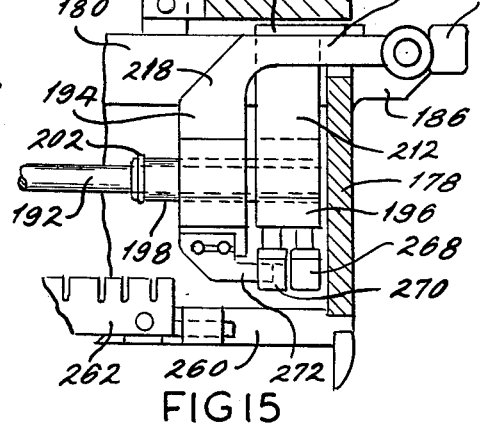
FIG. 15 is a sectional view taken along line 15—15 of FIG. 13 and showing the extractor and locator slides in elevation.

The extractor and locator slides 194 and 196 are propelled within the main block 175 by a horizontal drive screw 206 which is located between and parallel to the slide rods 192 and has its ends mounted in bearings located in the end walls 178 of the block 175. The screw 206 threads through a nut 208 in the extractor slide 194, but is not engaged with the locator slide 196. It is revolved by a D.C. stepping motor 210 which is mounted on the rear end wall 178 of the block 175. Thus, when the motor 210 revolves the horizontal screw 206, the extractor slide 194 will move along the slide rods 192, and the locator slide 196, being coupled to the extractor slide 194 through the sleeves 198 and springs 204, will move in unison with the extractor slide 194, except when the locator slide 196 comes against the front end wall 178 of the block 175 (FIGS. 13 - 15). When this occurs, the locator slide 196 is at rest, but the extractor slide 194 is free to advance still further toward the front end wall 178 against the force exerted by the springs 204.

Figure 17:
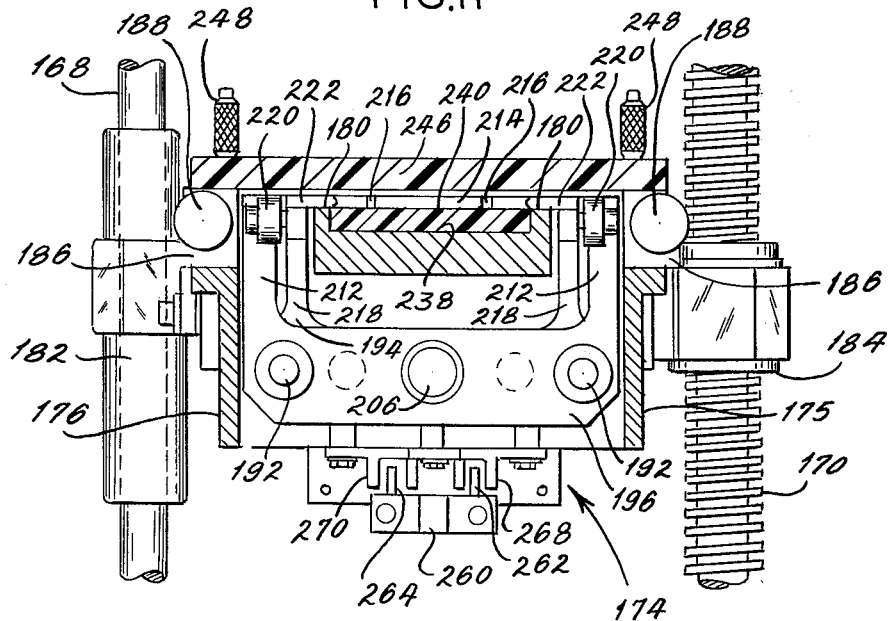
FIG. 17 is a sectional view of the reader head taken along line 17—17 of FIG. 14.

The locator slide 196 is provided at its sides with arms 212 (FIGS. 15 & 17) which project upwardly through slots in the top wall 180 of the main block 175. The upper ends of the arms 212 are connected by a positioning bar 214 (FIG. 13) which extends over the planar upper surface of the top wall 180. Indeed, the bar 214 slides on that planar upper surface as the locator slide 196 moves to and fro, on the slide rods 192. Along its forward margin the positioning bar 214 is provided with two prongs 216 which project forwardly toward the holder unit H and align with the positioning notches 4 in the cards C of that tray T which is in the reading position. However, even when the locator slide 196 is in its forwardmost position against the front end wall 178 of the block 175, the prongs 216 are backed off slightly from the positioning notches 4 of the cards C.

The extractor slide 194 has arms 218 (FIGS. 15 & 17) which are located below the positioning bar 214 of the locator slide 196 and project forwardly between the two arms 212 of that slide, with the upper surfaces of the arms 218 being located immediately below the undersurface of the bar 214. The arms 218 project beyond the forward margin of the positioning bar 214 where they are provided with rollers 220 which rotate about horizontal axes and align with the front flange 136 on the tray T. Indeed, when the extractor slide 194 is in its forwardmost position, the rollers 220 bear against the front flange 136 (FIG. 13). The arms 218 also carry gripping claws 222 which project inwardly toward each other and are at the same elevation as the prongs 216 on the positioning bar 214. The size of the claws 222 is such that they are capable of being loosely received in the gripping slots 6 on the sides of the cards C, and their positioning is such that they vertically align with the gripping slots 6 of the fully inserted cards C when the rollers 120 of the slide 194 bear against the front flange 136 of the tray T. Since the two slides 194 and 196 have the capability of moving relative to each, so do the claws 222 and the prongs 216 which are carried by those slides. Moreover when the slides 194 and 196 are spread farthest apart, that is when the extractor slide 194 is against the ring clips 202 on the sleeves 198 of the locator slides 196, the minimum spacing exists between the prongs 216 and the claws 222. This minimum spacing is less than the spacing between the positioning notches 4 and gripping slots 6 on the cards C. This feature, coupled with the fact that the locator slide 196 has the capability of moving relative to the extractor slide 194, enables the two slides 194 and 196, operating in unison, to engage or grip a card C in that tray T which is facing the reader unit R, extract that card C from the tray T, move the extracted card C over the upper surface of the main block 175 (FIG. 19), and then reinsert the card C back into the tray T.

To extract the first or uppermost card C from the tray T, the reader head 174 is positioned by the vertical drive screw 170 such that the positioning prongs 216 and gripping claws 222 are located slightly above the first card C. The horizontal drive screw 206 is furthermore run forwardly until the rollers 220 on the extractor slide 194 bear lightly against the front flange 136 on the tray T. When the extractor slide 194 is so disposed, the gripping claws 222 will be located directly above the gripping slots 6 in the card C. As the rollers 220 on the extractor slide 194 approach the front flange 136 on the tray T, the locator slide 194 will come to rest against the front end wall 178. The extractor slide 194 however will continue to move forwardly toward the stopped locator slide 194, in which case the spacing between the prongs 216 and claws 222 is increased and the coil springs 204 are compressed. When the locator slide 196 is at rest against the front wall 178, the prongs 216 are located generally above the notches 4 in the card C, but the leading edges of the prongs 216 are backed off slightly from the back edges of the notches 4.

Next the entire reader head 174 is lowered slightly by rotating the vertical drive screw 170 in the proper direction. This drops the positioning prongs 216 into the positioning notches 4 of the card C and simultaneously drops the gripping claws 222 into the gripping slots 6 (FIG. 13). Thereupon, the horizontal drive screw 206 is rotated to move the slides 194 and 196 rearwardly. During the initial rotation of the screw 206, the locator slide 196 remains stationary against the front end wall 178 of the block 175 but the extractor slide 194 moves backwardly, causing the gripping claws 222 to withdraw the card C. Indeed, the claws 222 move the card C into snug engagement with the positioning prongs 216 which fit into the notches 4. The springs 204 between the two slides 194 and 196 urge the prongs 216 snugly into the notches 4, and once the prongs 216 bottom out in the notches 4, the two slides 194 and 196 move in unison away from the front end wall 178 of the main block 180 with the driving force for the locator slide 194 being transmitted through the card C from the extractor slide 194 (FIG. 19). The prongs 216, which are in effect spring loaded with respect to the claws 222 as a result of the force exerted by the coil springs 204, maintain the card C properly oriented with respect to reader head 174. The card C is withdrawn a predetermined distance, and then the stepping motor 210 is reversed to reinsert the card C back in the tray T. The opposite sequence occurs during insertion, so that when the card C is fully inserted, the rollers 220 are against the front flange 136 of the tray T, the gripping claws 222 are loosely disposed in the gripping slots 6, and the positioning prongs 216 are backed off slightly from the positioning notches 4 as a result of the locator slide 196 having bottomed out against the front end wall 178 of the block 175. This frees the reader head 174 so that it can drop downwardly to grip the second card C.

The stepping motor 172, which rotates the vertical drive screw 170, is controlled through the computer K by an optical switch 230 (FIGS. 5 & 13) which is mounted on a bracket 232 attached to the main block 175. The switch 230 is a bifuricated device which is positioned such that the space between its two tines aligns with the left side of the front flange 136 on the tray T, so that as the reader head 174 descends, one tine will be opposite the front face of the flange 136 and the other tine will be opposite the back face. One of the tines carries a light emitting diode, while the other carries a photo-transistor. The latter is illuminated by the former through the locating apertures 148 in the left side of the flange 136. When the reading head 174 descends, the system works on the light-dark-light interrupt principle. Thus, above the flange 136 the photo-transistor will be illuminated by the emitter diode (light), but as the head 174 moves downwardly, the flange 136 will interrupt that light (dark), and finally at the first aperture 148 the transistor will again be illuminated (light), causing the motor 172 to stop it. This positions the head 174 with its positioning prongs 116 and gripping claws 222 located slightly above the first card C. After the slides 194 and 196 move forwardly, the head 174 is moved to the second locating aperture 148 in the same light-dark-light interrupt sequence, and as a result the claws 222 will drop into the slots 6 of the first card C, whereas the prongs 116 will drop into the positioning notches 4 so that the first card C may be withdrawn and replaced in the manner previously described.

The computer K counts the number of locating apertures 148 observed by the optical switch 230 and after the last card C has been withdrawn and replaced, the head 174 is moved downwardly one more increment to the last aperture 148, at which position the gripping claws 122 are below lowermost card C. Thereupon the computer energizes the horizontal motor 210 so that it moves the slides 194 and 196 rearwardly to withdraw the gripping claws 122 and positioning prongs 116 back into the head 174. Then the computer K reverses the motor 172 to move the reader head 174 upwardly without stopping at each slot 144. Again, the computer counts the number of apertures 148 observed by the optical switch 230 and after the last aperture 148, the motor 172 continues to elevate the reading head 174 until the optical switch 230 reaches a stop tab 234 (FIG. 5) which is mounted on the top piece 164 of the frame 160. The tab 234 interrupts the beam of light emitted by the diode of the switch 230, and the signal so generated at the photo-transistor causes the computer K to stop the motor 172 and to further, at a prescribed time thereafter, index the carrousel 76 of the card holder unit H.

The top wall 180 of the main block 175 on the reader head 174 has a recess 238 (FIGS. 13, 14 & 17) which opens out of its planar top surface, and the recess contains a detection plate 240 which lies flush with the planar upper surface. The plate 240 contains an array of seven digit sensing emitters 242 (FIG. 13) which are arranged generally in the configuration of the numeral 8. This array is furthermore positioned such that identification segments 24, 26 and 28 will pass over them. The segments 24 and 28 are in the shape of a block numeral 8, and when any of those segments are directly over the array, a different emitter 242 will be under each of the seven bars of the segment 24 or 28. Furthermore, some of the emitters 142 will align with the code segments 26 emitters. The dielectric plate 240 also contains five well sensing emitters 244 which are arranged in a row oriented transversely of the direction of horizontal translation for the slides 194 and 196. The spacing between the emitters 244 equals the spacing between the viewing wells 16 in the several rows of the identification cards $C_1$. The positioning is such that as an identification card $C_1$ is moved over the plate 240 by the extractor slide 194, the rows of viewing wells 16 therein will successively pass over the row of emitters 244. When any row of viewing wells 16 is over the row of well sensing emitters 244, the emitters 244 will precisely align with the wells 16 and the light emitted by them will project through the wells 16. When a sensitively card $C_s$ is passed over the plate 240, four of the five well sensing emitters 244 align with the four wells 16 in each row of that card. The emitters 244 should preferably emit light having a wave length of 660 nanometers.

Directly opposite from the dielectric plate 240 is another dielectric plate 246 (FIGS. 12, 17 & 19) which is hinged to the main block 175 such that it may be moved from an elevated position in which it is generally vertical to a lower operating or reading position wherein it is horizontal and parallel to the plate 240. When the plate 246 is in its lower position, the spacing between the two dielectric plates 240 and 246 is slightly greater than the thickness of the cards C. The plate 246 is precisely positioned in its lower position by locating pins 248, and is secured in that position by over-center hooks 249. The dielectric plate 246 contains a separate digit detector 250 (FIG. 17) for each digit sensing emitter 242, with the detectors 250 being precisely aligned with the corresponding emitters 242 across the space between the plates 240 and 246. Hence, the detectors 250 recognize light projected by the emitters 242. The plate 246 further contains well detectors 252 which aligns with the well emitters 242 so as to detect light projected from the emitters 244 and measure the intensity thereof. Each detector 250 and 252 constitutes at least one photo-transistor, and preferably more as explained in co-pending application Ser. No. 682,728 of R. A. Charles, D. W. Jones, J. L. Staples, and J. R. Wieger, filed May 3, 1976 and entitled MACHINE AND PROCESS FOR READING CARDS CONTAINING MEDICAL SPECIMENS. The detectors 250 and 252 are connected with the computer K which correlates and analyzes the readings derived therefrom.

Attached to the lower end of the main block 175 on the slide 174 is a bracket 260 (FIGS. 16 & 17) which carries two control bars 262 and 264. Each bar 262 and 264 extends parallel to the slide rods 192 and each contains a plurality of upwardly opening notches 266. The bar 262 is monitored by an optical switch 268 (FIGS. 15 & 17) which is attached to the underside of the locator slide 196, while the bar 264 is monitored by an optical switch 270 which is also attached to the locator slide 196. The switch 268 has a light emitting diode on one side of the bar 262 and a phototransistor on the other, with the two being positioned such that light from the former falls on the latter only when a notch 266 is between the two. The optical switch 270 likewise has a light emitting diode and phototransistor with the latter normally being obscured from the former by the bar 264, except when a notch 266 is between the two. Both optical switches 268 and 370 are connected with the computer K.

The bar 262 and its optical switch 268 control the withdrawal of the cards C from the tray. In this regard, the first notch 266 of the bar 262 is positioned such that the phototransistor of the switch 268 will be exposed to the light emitting diode of that switch before the first identification segment 24 arrives at the opposed array of digit emitters 242 and digit detectors 250. The remaining notches 266 of the bar 262 are positioned such that the optical switch 268 will be located at them each time an identification segment 24, 26 and 28 lies directly over the arrays of digit emitters 242. Moreover, the computer K is programmed to stop the horizontal stepping motor 210, and thereby stop the extractor and locator slides 194 and 196, each time the optical switch 268 provides a signal at one of the notches 266. The interval during which the motor 210 is de-energized is extremely short, it being on the order of 0.020 seconds, and during this interval a reading is obtained from the array of digit detectors 250. The motor 210 moves the slides 194 and 196 successively from one notch 266 to the next along the length of the bar 262. The reading obtained at the first notch 266 is for calibration purposes so that compensation may be made for variations in the light transmitting characteristics, of the various plastic materials from which the cards C may be molded. This reading establishes a threshold, and all readings must surpass this threshold before a marking is considered to exist between any emitter 242 and its corresponding detector 250. The next reading occurs at the identification segment 24, and the computer K translates this reading into the numeral corresponding to the blocked out portions of the segment 24. The next set of readings are obtained from the code segments 26, which indicate the type of card C being analyzed. The last set of readings are at the series of identification segments 28, and these readings are translated by the computer K into the patient identification number.

Once the optical switch 268 reaches the last notch 266, the computer K reverses the stepping motor 219 and thereafter the control is assumed by the bar 264 and its optical switch 270. The notches 266 are arranged in the bar 264 such that a notch 266 will be located at the switch 270 each time a row of viewing wells 16 aligns with a row of well emitters 244 and its corresponding row of well detectors 252. Moreover, each time this occurs the computer K will stop the motor 210 for a short interval on the order of 0.020 seconds so that a reading may be acquired. The reading of each well detector 252 is of course a measure of the intensity of light falling upon the detectors 252 and that reading reflects amount or character of light passing through the viewing well 16 which is being monitored. Of course, wells 16 of an entire row are monitored each time the optical switch 270 is located opposite a notch 266 in the bar 264. The motor 210 does not stop at the end of the control bar 264, but instead continues to rotate until a tab 272 (FIGS. 12 & 15) carried by the extractor slide 194 projects into the switch 270 and blocks the beam of light emitted by its diode. This occurs after the locator slide 196 bottoms out against the front wall 178 of the block 175 and the extractor slide 194 has continued to move forwardly until the rollers 220 are again located against the flange 136 of the tray T (FIG. 13).

OPERATION

The first step in utilizing the automated microbial analyzer A is to select the card C appropriate for the specimen. For example, if a urine specimen is being tested, a urine card is selected. This card C is identified by an opaque marking in one of the code segments 26 (FIG. 2). The proper card C, having been selected, is inserted between the guide webs 38 of the loading device L and is advanced until the needles 40 and 42 project completely through the septa 12 in the card C (FIG. 4). Thereafter a prescribed amount of saline solution is introduced into the tubes 34 and 36 of the loading device L, and the specimen is introduced into this saline solution, forming a known dilution. The dilution in the long tube 36 is weaker than that in the short tube 34. Thereupon the flexible stacks 44 having the cotton wads 46 therein are installed over the tops of the tubes 34 and 36 to prevent the entry of foreign matter.

The loading device L having card C attached to it (FIG. 4) is inserted into a vacuum chamber (not shown) from which air is evacuated until the pressure within the chamber equals approximately 28 inches Hg. As the pressure is reduced, the air within the interior of the card C escapes, this air bubbling through the dilutions in the tubes 34 and 36. When the appropriate pressure is achieved, the vacuum is released so that atmospheric pressure will again bear against the top of the dilution columns in the tubes 34 and 36, and this forces the dilutions into the cards C. In particular, the dilutions flow into the receiving chambers 14 and thence into the filling channels 20 and 22 from which it is discharged into the viewing walls 16. Any entrapped air tends to accumulate in the overflow channel 18 since they are projected upwardly. The dilution rehydrates the culture media in the viewing wells 16. Thereupon the dilution is poured from the loading device D and the card C is detached.

Before the card C is subjected to any further processing, the patient identification number is marked on it by filling in the appropriate bars of the various identification segments 28 and 24. Since each identification segment 24 is in the configuration of the block numeral "8", any numeral may be formed merely by selecting the appropriate bars to blank out. The markings are made with a felt tip pen which for all intents and purposes makes an opaque mark on the stippled surfaces of the segments 24 and 28. The markings of the code segments 26 are already on the card C they having been applied at the factory to indicate the type of card C.

Following the marking and loading of the card C, the card C is inserted into a tray T (FIG. 1). Since the card C is to be utilized in a large-scale screening process, it will be one of many cards C, each one occupying a different slot 144 in the tray T. The keys 146 along the fins 142 of the tray T prevent the cards from being installed in any position except the correct position. In that position the kerf 8 of the card C fits into the key 146 along the card receiving slot 144, and the positioning notches 4 and the gripping slots 6 are located at a prescribed distance beyond the front flange 136 of the tray T.

Figure 10:
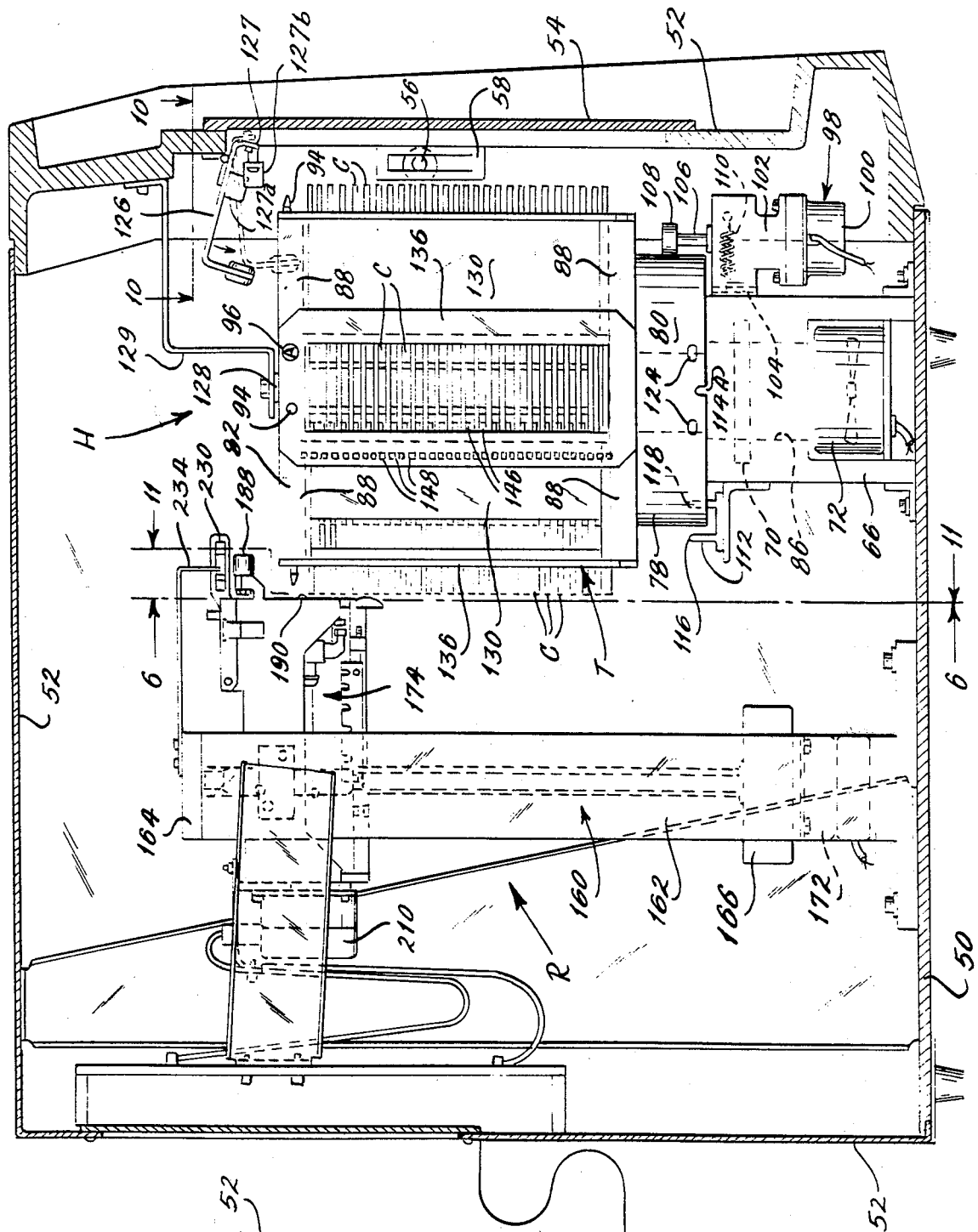
FIG. 10 is a sectional view taken along line 10—10 of FIG. 5 and showing the restraining element for preventing rotation of the carrousel when the cabinet door is open.
Figure 10:
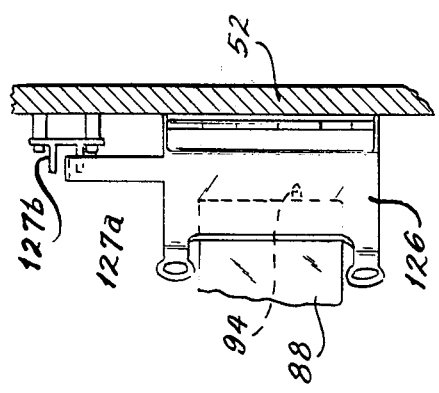

When the tray T is fully loaded, it is installed on the carrousel 76 of the card holder H, this being achieved by opening the door 54 of the cabinet D and merely inserting the tray T into the grooves 90 of the two retaining arms 88 which are presented toward the door 54 (FIG. 1). In this connection, it should be noted that the lock 56 prevents the door 54 from being opened when the carrousel 76 is being indexed, and likewise when the reader unit R is traversing a row of cards C on another tray T. Moreover, when the door 54 is opened, it releases the tab 127 of the retaining element 126 so as to permit the retaining element 126 to drop downwardly and engage the upper retaining arm 88 presented toward the door 54 (FIGS. 5 & 10). This prevents the carrousel 76 from being rotated as a tray T is inserted into it. As the tray T is inserted between the two retaining arms 88, the locating pin on the upper arm 88 fits into the hole 138 in the front flange 136 of the tray T so as to properly locate the tray T on the carrousel 76 (FIGS. 6 & 7). The roller detents 92 moreover project into the apertures 134 in the end walls 132 of the tray T to retain the tray T in place. The door 54 is thereupon closed.

The fan 72 of the card holder H directs a stream of air upwardly across the heater element 70, and this stream of heated air passes upwardly into the stack 84 from which it is discharged through the horizontal slots 86 in the stack 84. These slots open into the trays T and are offset from the cards C within the trays T. As a result the heated air passes over the upper and lower surfaces of the cards C so as to elevate the temperature of the cards C to a prescribed value suitable for incubating any microorganisms in the viewing wells 16. This temperature should be about 35° C. and is maintained at a substantially constant value by the thermocouple probe 128. The tray T which is loaded through the door 54 is incubated for about one-half hour before the cards C are extracted therefrom and read. During this time the carrousel 76 rotates 90°, positioning the tray T in a lateral position, and after 15 minutes in the lateral position, the carrousel 76 rotates another 90° positioning the tray T in the reading position opposite the reader unit R.

The indexing is initiated by the computer K which energizes the motor 100 (FIG. 5), causing it to rotate the carrousel 76 until the next notch 114 is observed by the optical switch 112. At this point the motor 100 is deenergized and rotation ceases. The optical positioning switches 120 and 122 (FIG. 6) provide the computer K with signals which reflect the arrangement of apertures 124 at the particular notch 114 where the carrousel 76 stops, and the signals enable the computer to determine which of the four trays T is in the reading position.

After the tray T reaches the reading position, the computer K energizes the drive motor 172 which rotates the drive screw 170 and causes the reader head 174 to descend from its uppermost position (FIG. 5) opposite the stop tab 234. The reader head 174 descends until the optical switch 230 senses the upper edge of the front flange 136 on the tray T. Thereupon, the motor is reversed for a short duration and a calibration reading is taken for the switch 230, which is used by and stored in the memory of the computer K to establish a threshold value which must be surpassed to indicate the presence of a locating aperture 148 in the tray flange 136. The motor 172 is again energized to lower the head 174, and the head 174 descends until the switch 230 is opposite the first locating aperture 148, at which time the motor 172 stops. In this regard, the control circuit for the motor 172 is of the light-dark-light interrupt variety. Thus, the optical switch 230 observes light before the upper margin of the tray T, then dark as it passes over the upper margin, and then light again at the first locating aperture 148. During the descent the rollers 188 on the block 175 of the reader head 174 engage the side edges of the front flange 136 on the tray T so as to precisely position the tray T opposite the reading head 174. Moreover, the front roller 190 will have forced any outwardly projecting cards C into their fully inserted positions.

When the optical switch 230 arrives at the first aperture 148, the computer K not only stops the vertical motor 172, but further energizes the stepping motor 210 which drives the horizontal drive screw 206 and causes the slides 194 and 196 to move forwardly toward the tray T until the horizontal stop tab 272 interrupts the beam projected by the optical switch 264, at which time motor 210 stops. This positions the extractor slide 194 with its rollers 220 against the front flange 136 of the tray T. When the extractor slide 194 is so disposed, the locator slide 196 is against the front wall of the main block 175. Moreover, the gripping claws 222 on the extractor slide 194 are located directly above the gripping slots 6 on the first card C, while the prongs 216 on the positioning bar 214 of the locator slide 196 are located directly above the positioning notches 4 in that card C, but their leading margins are offset slightly to the rear of the bases of the notches 4.

After the extractor slide 194 moves to its forwardmost position, the computer K again energizes the stepping motor 210 which lowers the reader head 174 until the optical switch 230 comes to the next or second aperture 148, at which time the motor 210 again stops. As the rending head 174 descends, the gripping claws 222 drop into the gripping slots 6 of the card C, while the locating prongs 216 drop into the positioning notches 4 (FIG. 13). Thereupon, the computer K energizes the horizontal stepping motor 210 which drives the horizontal drive screw 206 such that it moves the extractor slide 194 away from the tray T. During the initial increment of movement the locator slide 196 remains against the front end wall 178 of the block 175, and as a result the gripping claws 222 move toward the positioning prongs 216. The claws 222, being engaged with the card C, move the entire card C toward the prongs 216 and cause the prongs 216 to bottom out against the bases of the positioning notches 4. When this occurs, the locator slide 196 will move with the extractor slide 194 and the springs 204 will cause the prongs 216 to bear against the card C at the notches 4. This not only maintains the gripping claws 222 in engagement with the card C at the notches 6, but further orients the card C in the correct lateral and angular disposition with respect to the reader head 174. The two slides 194 and 196, acting in unison, cause the card C to be withdrawn from the tray T and to pass between the dielectric plates 240 and 246 on the main block 175.

The optical switch 268 is carried by the locator slide 196, and when this switch reaches the first notch in the control bar 262, the signal which is generated causes the computer K to stop the horizontal motor 210 for an instant. When this occurs, opposed arrays of digit emitters 242 and digit detectors 250 will be ahead of the leading ientification segment 24 on the card C, and the emitters 242 will project through a transparent portion of the card C. This calibrates the circuitry, establishing a threshold value, beyond which a reading must pass in order to indicate a marking on the card C. The calibration compensates for variations in the light transmitting capabilities of various plastics from which the cards C may be molded. The interruption at the first notch 266 is momentary, and the motor 210 is again energized, until the optical switch 268 comes to the second notch 266 in the control bar 262. At this notch 266 another momentary hesitation occurs and the digit emitters 242 project light through the card C at the identification segment 24 thereon. This segment is in the shape of a block letter "8" and any bars of it which are blanked out to form a numeral will interrupt the light directed toward the digit detectors 250 behind those bars. As a result, only the bars which are left blank will pass sufficient light to enable the detectors 250 located beyond them to pass the threshold value. On this basis the computer K determines the number appearing in the first identification segment 24. The next set of notches 266 momentarily stop the slides 194 and 196 such that the code segments 26 are located opposite the digit emitters 242 and digit detectors 250. The readings derived at these momentary hesitations enable the computer K to determine the type of card C being extracted from the tray T. The remaining notches 166 stop the slides 194 and 196 such that the identification segments 28 align with the opposed arrays emitters 242 and detectors 250. Each reading represents a numeral and these numerals provide the computer with the identification number of the patient from whom the specimen was obtained.

Upon completion of the reading interval at the last notch 266 of the bar 262, the computer reverses the stepping motor 210, (FIG. 19). The drive screw 206 thereupon moves the slides 194 and 196 in the opposite direction. As a result, the card C is moved back into the slot 144 from which it was withdrawn. Moreover, upon the return of the slides 194 and 196, the control is transferred to the optical switch 270 and its control bar 264. The optical switch 270 reaches the first notch 266 in the bar 264 when the first row of viewing walls 16 is between the well emitters 244 and well detectors 252. Here the computer K momentarily stops the motor 210 so that a reading of the first row of wells 216 may be obtained. This reading results from the projection of light emitted by the well emitters 244 through the viewing wells 16. The intensity of the light falling on the well detectors 252 located beyond the wells 16, indicates the light transmitting capabilities of the viewing wells 16. Thus, an increase in turbidity or a color change in a well 16 will reduce the light transmitting characteristics of the well 16, and the detector 252 which monitors that well 16 will supply a different signal to the computer K. After the momentary hesitation at the first notch 266 of the bar 264 the motor 210 moves the slides 194 and 196 until the switch 270 comes to the second notch 266, and at this time the well emitters 244 and well detectors 252 read the second row of viewing wells 16. Momentary hesitations are made at the third and fourth rows of the viewing wells 16 in the manner previously described, and readings are provided reflecting the light transmitting characteristics of those wells 16. After the fourth row of wells 16 is read, the motor 210 continues to operate until the horizontal stop tab 272 passes into and interrupts the light projected by the switch 268. When this occurs, the computer K stops the motor 210. The extractor slide 194 will at this point have its rollers 220 located against the front flange 136 of the tray T, while the locator slide 196 will be against the front end wall 178 of the main block 175 with its prongs 116 released from the card C so that they no longer fit snugly in the positioning notches 4 (FIG. 13).

Once the first card C is returned to its fully inserted position within the tray T, the computer K again energizes the stepping motor 172 which turns the vertical drive screw 170 and lowers the viewing head 174 until the optical switch 230 comes to the next locating aperture 148 in the flange 136 of the tray T. As the viewing head 174 descends, the gripping claws 122 move out of the gripping slots 6 of the first card and drop into the gripping slots 6 of the second card C. Likewise, the prongs 216 of the locator slide 196 move from the positioning notches 4 of the first card C to the positioning notches 4 of the second card C. Thereupon the stepping motor 210 is energized to move the extractor and locator slides 194 and 196 rearwardly and then forwardly again. The same reading sequence occurs, that is, the identification segments 24, 26 and 28 are read as the card C is extracted, whereas the viewing wells 16 are read as the card C is reinserted.

The foregoing procedure is repeated for each card receiving slot 144 in the tray T. Even though no card C exists within a card receiving slot, the slides 194 and 196 nevertheless make their to and fro translation, but the absence of any readings on the rearward translation will indicate the absence of a card, so the computer K will not record any information. The computer K counts the number of locating apertures 148 and when that number corresponds to the total number at apertures 148, in which case the optical switch 230 is opposite the lowermost aperture 148, the motor 210 retracts the slides 194 and 196 and the motor 172 elevates the reader head 174 without interruption. In other words, at the bottom locating aperture 148, the motor 210 moves the slides 194 and 196 rearwardly past the leading edges of the cards C. When the motor 172 is energized to raise the reader head 174. Again the computer K counts the number of locating apertures 148 and after the uppermost aperture 148 the optical switch senses a relatively long void space, indicating to the computer that the optical switch 230 is beyond the upper margin of the tray flange 136. The motor 172 continues to run until the optical switch 230 reaches the vertical stop tab 234 (FIG. 5). At this point the motor 172 stops and the reader head 174 is located sufficiently above the tray T to permit indexing of the carrousel 76.

The time necessary to read a tray of 30 cards C is about 6 minutes. The computer K however does not index the carrousel 76 at the end of this 6 minute period, but instead allows the carrousel 76 to remain at rest for another 9 minutes. During this 9 minute period the computer K extinguishes the read light 60 and de-energizes the solenoid lock 56 so as to allow access to the door 54. Hence, during this 9 minute interval the door 54 may be opened and a new tray T may be placed between the retaining arms 88 located directly opposite the door 54. Also, individual cards C may be withdrawn from the tray T presented toward the door 54 or new cards may be inserted into any empty slots 144 located in that tray T. This is in contrast to the 6-minute period when the solenoid lock 58 is energized and the read light 60 is illuminated. During this period, the door 54 is closed, so that the tray T presented toward the door 54 is inaccessible.

At the end of the 9-minute period, the computer K energizes the motor 100 of the holder unit H and that motor revolves the carrousel 76 until the next notch 114 comes to the optical switch 112. The apertures 124 located at this notch 114 will be different than those at the previous notch 114; as a result the computer K will be informed through its optical positioning switches 120 and 122 as to which tray T is located in the read position. The same extraction, read, and replacement sequence is repeated for the cards C at the next tray T.

Since the carrousel 76 indexes 90° every 15 minutes, each tray T will pass through the reading position at the reader unit R once every hour. Hence each card C is read once every hour. Any wells 16 in an identification card C, which shows a decrease in its light transmitting characteristics through successive readings contain the microorganism to which the culture medium in that well 16 is specific, thus indicating the presence of that microorganism in the specimen. Usually a card C is kept in the holder unit for 13 hours. Any change in light transmitting should be clearly descernible from the 13 readings taken during this period.

The antibiotic sensitivity cards $C_s$ are normally loaded after the specimen has been analyzed with an identification card Ci and as a result of the analysis is found to contain a harmful microorganism. Sensitivity cards $C_s$ are then selected, these cards having antibiotics mixed into the culture media in the wells 16 thereof, and these antibiotics are likely to be effective against the particular microorganism. The sensitivity cards $C_s$ are loaded with the specimen in the same manner and are likewise handled by the analyzer A in the same manner as previously described, however, the absence of a change in light transmitting characteristics of any wells 16 indicates that the antibiotic in that well 16 is effective against the harmful microorganism in the specimen. The same patient identification number is marked on the identification segments 28 of the sensitively cards $C_s$, but these cards $C_s$ may be distinguished from the identification card Ci, as well as from each other in the computer report by a further identification number marked on the single identification segment 24.

The operations which have heretofore been described as computer controlled may be initiated by an individual, but this would result in a substantial lessening in the degree of automation.

This invention is intended to cover all changes and modifications of the example of the invention herein chosen for purposes of the disclosure which do not constitute departures from the spirit and scope of the invention.

What is claimed is:

1. A machine for examining cards which are normally stored in a card holder and have viewing wells therein; said machine comprising: a mounting element; a card holder positioned adjacent to the mounting element, said card holder being capable of holding a plurality of cards therein with the cards being presented to the mounting element; extracting means on the mounting element aligned with the card holder for gripping the cards individually and withdrawing them from the card holder; light emitting means on the mounting element for projecting light through the wells when the cards are withdrawn from the card holder; light detecting means on the mounting element for determining the intensity of light passing through the wells; and means for aligning the wells in the cards in registry with the light emitting means and with the light detecting means.

2. A machine according to claim 1 wherein the means for gripping the cards and withdrawing them further reinserts the cards into the holder.

3. A machine according to claim 1 and further comprising means on the mounting element for detecting and reading indicia placed on the card.

4. A machine according to claim 3 wherein the means for detecting indicia includes an optical array comprised of light emitters arranged in a FIG. 8 and light detectors aligned with the individual emitters, the emitters being located opposite one face of the card as it is withdrawn and the detectors being located opposite the opposite face.

5. A machine according to claim 4 wherein the means for detecting the indicia further comprises optical switch carried by the extracting means, and a control bar mounted in a fixed position on the mounting element and having cutouts at which the optical switch its located when the light emitters and detectors align with indicia on the card so as to produce a signal each time that the light emitters and detectors are aligned with inidica.

6. A machine according to claim 1 wherein each card has gripping slots opening out of its is side edges, and the extracting means has gripping claws which fit into the slots and move away from the holder to withdraw the card from the holder.

7. A machine according to claim 6 wherein the machine has positioning surfaces which bear against the end of the card as the gripping claws withdraw the card, the gripping claws moving the card into snug engagement with the positioning surfaces so as to enable the positioning surfaces to correctly orient the card with respect to the mounting element.

8. A machine according to claim 7 wherein the positioning surfaces are prongs which fit into notches in the end of the card.

9. A machine according to claim 6 wherein the claws are fixed in position with respect to each other; and further comprising means for moving the mounting element generally perpendicular to the direction in which the cards are withdrawn from the holder to enable the claws when aligned with the gripping slots to move into the slots.

10. A machine according to claim 9 wherein the extracting means comprises an extractor slide mounted on the mounting element and having the gripping claws thereon, and means for moving the extractor slide toward and away from the holder.

11. A machine according to claim 10 wherein the extracting means further comprises a locator mounted on the mounting element and movable relative to the extractor slide, the locator having a positioning surface thereon which bears against an end edge on the extractor slide to properly position the card as it is withdrawn by the gripping claws, and a spring positioned between the locator and extractor slide such that it urges the positioning surface snugly against the end of the card.

12. A machine according to claim 11 wherein the locator is a slide which moves relative to the extractor slide with the direction of the relative movement being parallel to the direction of movement of the extractor slide on the mounting element.

13. A machine according to claim 12 wherein the means for moving the extractor slide comprises a motor on the mounting element, and a drive screw turned by the motor and threaded through the extractor slide so that rotation of the drive screw will cause the extractor slide to move.

14. A machine according to claim 11 wherein the mounting element carries a stop surface against which the locator bears when the gripping claws initially fit into the gripping slots of the card so that the positioning surface will not bear against the end of the card when the gripping claws are inserted into the gripping slots, the locator being withdrawn from the stop surface as the extractor slide withdraws the card, so as to enable the positioning surface on the extractor slide to bear against the end of the card.

15. A machine for examining flat cards which are arranged in a holder parallel to each other with their flat major surface areas parallel and the side and end margins in registration, the cards being formed from a transparent material and having viewing wells arranged in transverse rows thereon and identification segments thereon on which opaque markings may be made, the cards further having gripping slots opening out of the sides thereof; said machine comprising: a base; an upstanding frame mounted on the base opposite the holder; a block supported on the frame; vertical drive means for moving the block upwardly and downwardly on the frame; an extractor slide on the block and having gripping claws thereon with the claws being positioned and sized to fit into the gripping slots on the cards; horizontal drive means for moving the extractor slide horizontally toward and away from the holder so that a card engaged by the gripping claws will be withdrawn from the holder and moved over the block; an array of first light emitters located on the block such that the identification segments will pass by them, the first emitters being oriented such that the light emitted thereby is projected toward the one major surface area of the card as it is withdrawn; an array of first light detectors located on the block and aligned with the first emitters, the first detectors facing the opposite major surface of the card as the card is withdrawn so as to detect any light from the emitters which pass through the identification segments; second emitters located on the block such that they align with the viewing wells of each row in succession as the card is moved relative to the block; second light detectors on the block and aligned with the second light emitters, the second light detectors being positioned such that the card as it is withdrawn passed between the second emitters and the second detectors, whereby the second detectors measure the intensity of light passing through the wells.

16. A machine according to claim 15 and further comprising a locator slide movable relative to the extractor slide and having a positioning surface thereon which aligns with the end of the card, and a spring between the extractor and locator slides and urging the positioning surface of the locator slide toward the end of the card when the card is engaged by the gripping claws so as to properly orient the card with respect to the block.

17. A machine according to claim 16 wherein the block has a stop surface against which the locator slide bears when the gripping claws initially move into the gripping slots of the card, the stop surface being positioned such that the positioning surface is backed off slightly from the card so as not to interfer with the card as the gripping claws move into the gripping slots, the extractor slide moving the card into snug engagement with the positioning surface as the horizontal drive means causes the extractor slide to withdraw the card from the holder and the locator slide thereafter moving with the extractor slide.

18. A machine according to claim 17 and further comprising first and second optical switches on the locator slide, and first and second control bars on the block along the paths taken by the first and second optical switches, respectively, as the locator slide moves, the control bars having cutouts therein which enable the respective switches to project light past the bars and thereby provide a signal for controlling the horizontal drive means, the cutouts on the first bar being arranged to stop the drive means each time an identification segment on the card aligns with the first emitters and detectors, the cutouts on the second bar being arranged to stop the drive means each time a row of wells aligns with the second emitters and detectors.

19. A machine according to claim 15 and further comprising control means on the block for controlling the vertical drive means such that vertical drive means stops each time the claws of the extractor slide move into the gripping slots of a card in the holder.

20. An apparatus for analyzing flat cards having viewing wells containing culture media and diluted biological specimens to determine if the specimens contain microorganisms; said apparatus comprising: a holder which holds a plurality of cards with one card being located after the other; extracting means for withdrawing the cards individually from the holder, and reading means on the extracting means for monitoring the viewing wells of each card when the card is withdrawn, to determine if the optical characteristics of the viewing wells change.

21. An apparatus according to claim 20 wherein the reading means comprises light emitters and light detectors arranged in pairs with the emitters being aligned with the detectors so as to illuminate the detectors, each pair of emitters and detectors being located such that a card as it is withdrawn from the holder will pass between them and wells in the card will come into registration with such pairs.

22. An apparatus accordng to claim 20 wherein the holder supports the cards parallel to each other with their margins in registration, and further comprising positioning means for moving the extracting means along holder to enable the plurality cards to be withdrawn individually, one after the other.

23. An apparatus according to claim 22 and further comprising first control means on the extracting means for controlling the positioning means to positin the extracting means such that it is capable of engaging the cards.

24. An apparatus according to claim 23 and further comprising second positioning means for stopping the extracting means when the wells of the cards are in registration with the pairs of emitters and detectors.

25. An apparatus according to claim 24 and further comprising means for detecting and determining the configuration of indicia placed on the cards.

26. An apparatus according to claim 20 wherein the holder supports several rows of cards with each row having the cards located therein parallel and in marginal registration; and further comprising indexing means for moving various rows such that each may be positioned opposite the extracting means, and positioning means for moving the extracting means parallel to the row positioned opposite to the extracting means so as to withdraw different cards from that row.

27. An apparatus according to claim 26 and further comprising a pedestal and a rotatable carrousel mounted on the pedestal and supporting the individual rows of cards, with the rows being spaced circumferentially around the carrousel, and wherein the indexing means rotates the carrousel on the pedestal to bring the various rows into an extracting position opposite the extracting means.

28. An apparatus according to claim 27 and futher comprising incubating means for maintaining the cards at a selected temperature.

29. An apparatus according to claim 27 wherein the carrousel includes a center stack around which the rows of cards are disposed and the center stack has apertures located adjacent to the ends of the cards; and further comprising means for introducing a heated airstream into the stack, whereby the heated air of the airstream will discharge through the apertures and incubate the biological specimens in the cards.

30. An apparatus according to claim 27 wherein the holder further comprises trays into which the cards fit with each tray containing a separate row of cards, and the trays fit into and are detachable from the carrousel so that they may be loaded remote from the carrousel.

31. A machine capable of holding a plurality of flat cards having wells containing culture media and diluted biological specimens to determine if the specimens contain viable microorganisms; said machine comprising a pedestal; a carrousel mounted on the pedestal to rotate about a fixed axis; retaining means on the carrousel for holding the cards stacked in rows parallel to the axis of rotation with the rows being spaced circumferentially around the axis of rotation and with the cards in each row being stacked parallel to each other and in marginal registration; drive means for rotating the carrousel relative to the pedestal; positioning means controlling the drive means to bring each row into a predetermined position at which the cards may be extracted from the retaining means; extracting means for extracting cards from the row of cards in said predetermined position; and reading means for ascertaining the optical characteristics of the wells in a card when it is extracted from the retaining means by the extracting means, said reading means comprising light emitters for projecting light though the wells and light detectors of determining the intensity of the light which passes through the wells.

32. A machine according to claim 31 wherein the carrousel contains a center stack around which the rows of cards are disposed, and the stack has apertures located adjacent to the ends of the cards, and further comprising means for introducing a heated airstream into the stack, whereby the heated air of the airstream is discharged from the apertures and passes over the cards so as to incubate any microorganisms in the culture media of the cards.

33. A machine according to claim 32 wherein the means for introducing a heated airstream includes a heater in he pedestal and a fan in the pedestal, the fan being directed to discharge air across the heater and into the stack of the carrousel.

34. A machine according to claim 31 wherein the carrousel has pairs of retaining arms at circumferentially spaced intervals, and the retaining means are located between the retaining arms of each pair.

35. A machine according to claim 34 wherein the retaining means comprises a tray between each pair of retaining arms, each tray comprising side and end walls, and fins in the side walls to define slots into which the cards fit.

36. A machine according to claim 35 wherein the fins along one side wall have keys which register which kerfs in side edges of the cards such that the cards may be inserted into the slots in only one orientation.

37. A machine according to claim 36 wherein each tray has a front flange presented away from the axis of rotation for the carrousel and the front flange has locating apertures along one side thereof, there being a separate aperture for each slot, the locating aperture for each slot being located in a predetermined position with respect to its respective slot to locate an extracting device opposite the slot so that the card may be withdrawn from the slot.

38. A machine according to claim 31 wherein the carrousel has a cylindrical skirt with cutouts therein, the spacing of the cutouts corresponding to the spacing between the rows of cards, and wherein the positioning means includes an optical switch which senses the cutouts and stops the drive means when such a cutout is sensed.

39. A machine according to claim 38 wherein the drive means includes a powered friction wheel which bears against the cylindrical surface of the skirt on the carrousel.

40. A machine according to claim 31 and further comprising means for identifying the row of cards which is presented in a predetermined direction.

* * * * *

UNITED STATES PATENT AND TRADEMARK OFFICE
CERTIFICATE OF CORRECTION

PATENT NO. : 4,118,280
DATED : October 3, 1978
INVENTOR(S) : Charles, et al

It is certified that error appears in the above-identified patent and that said Letters Patent are hereby corrected as shown below:

Column 11, line 13 after "threads" and before "this" insert "through"

Column 16, line 21 after "motor" cancel "219" and substitute therefor "210"

Column 21, line 10 after "." and before "the" cancel "When" and substitute therefor "Then"

Column 26, line 15 after "detectors" and before "determining" cancel "of" and substitute therefor "for"

Column 26, line 41, after "register" cancel "which" and substitute therefor "with".

Signed and Sealed this

Twenty-fourth Day of April 1979

[SEAL]

Attest:

RUTH C. MASON
Attesting Officer

DONALD W. BANNER
Commissioner of Patents and Trademarks